United States Patent
Miick et al.

(10) Patent No.: US 11,377,688 B2
(45) Date of Patent: Jul. 5, 2022

(54) COMPOSITIONS AND METHODS FOR DETECTING C1ORF43 NUCLEIC ACID

(71) Applicant: Gen-Probe Incorporated, San Diego, CA (US)

(72) Inventors: Siobhán M. Miick, San Diego, CA (US); Paul M. Darby, San Diego, CA (US); Jo Ann Jackson, Lakeside, CA (US); Damon Kittredge Getman, Poway, CA (US)

(73) Assignee: Gen-Probe Incorporated, San Diego, CA (US)

(*) Notice: Subject to any disclaimer, the term of this patent is extended or adjusted under 35 U.S.C. 154(b) by 75 days.

(21) Appl. No.: 16/763,387

(22) PCT Filed: Nov. 15, 2018

(86) PCT No.: PCT/US2018/061225
§ 371 (c)(1),
(2) Date: May 12, 2020

(87) PCT Pub. No.: WO2019/099629
PCT Pub. Date: May 23, 2019

(65) Prior Publication Data
US 2020/0399696 A1     Dec. 24, 2020

Related U.S. Application Data

(60) Provisional application No. 62/588,130, filed on Nov. 17, 2017.

(51) Int. Cl.
*C12Q 1/68* (2018.01)
*C12Q 1/6876* (2018.01)

(52) U.S. Cl.
CPC ..... *C12Q 1/6876* (2013.01); *C12Q 2563/107* (2013.01)

(58) Field of Classification Search
CPC .................................................... C12Q 1/68
USPC ........................................................ 435/6.1
See application file for complete search history.

(56) References Cited

U.S. PATENT DOCUMENTS

| | | | |
|---|---|---|---|
| 4,683,195 A | 7/1987 | Mullis et al. | |
| 2005/0118625 A1 | 6/2005 | Mounts | |
| 2009/0286249 A1 | 11/2009 | Becker et al. | |
| 2013/0317083 A1 | 11/2013 | Rigoutsos | |
| 2016/0017431 A1* | 1/2016 | Giannikopoulos | C12Q 1/6886 435/7.1 |
| 2018/0223380 A1* | 8/2018 | Lin | C12Q 1/706 |
| 2019/0161809 A1* | 5/2019 | Di Fiore | C12Q 1/6886 |
| 2019/0376128 A1* | 12/2019 | Skog | C12Q 1/6851 |
| 2020/0325526 A1* | 10/2020 | Sherwood | G01N 33/566 |

FOREIGN PATENT DOCUMENTS

| | | |
|---|---|---|
| WO | 2003106714 A1 | 12/2003 |
| WO | 2006063065 A2 | 6/2006 |
| WO | 2008016988 A1 | 2/2008 |
| WO | 2017017516 A1 | 2/2017 |

OTHER PUBLICATIONS

Scarlet et al, The Orthology Clause in the Next Generation Sequencing Era: Novel Reference Genes Identified by RNA-seq in Humans Improve Normalization of Neonatal Equine Ovary RT-qPCR Data, PLoS One. Nov. 4, 2015;10(11):e0142122. doi: 10.1371/journal.pone.0142122. eCollection 2015.*
Aptima Combo 2 Assay (Panther System), 43 pages (2017).
Aptima Mycoplasma genitalium Assay, 24 pages (2017).
Aptima Specimen Transfer Kit, 9 pages (2017).
Aptima Unisex Swab Specimen Collection Kit for Endocervical and Male Urethral Swab Specimens 3 pages (2016).
Aptima® Trichomonas vaginalis Assay (Panther® System), 27 pages (2017).
Eisenberg and Levanon, "Human housekeeping genes, revisited." Trends in Genetics, 29(10): 569-574 (2013).
Hayes and Li "An integrative framework for the identification of double minute chromosomes using next generation sequencing data." BMC Genetics, 16(2): S1 (2015).
PCT, International Search Report and Written Opinion for PCT/US2018/061225, dated Feb. 12, 2019.
Progensa PCA3 Urine Specimen Transport Kit, 4 pages (2015).
Scarlet et al., "The Orthology Clause in the Next Generation Sequencing Era: Novel Reference Genes Identified by RNA-seq in Humans Equine Ovary RT-qPCR Data" PLOS One, 10(11): e0142122 (2015).
ThinPrep 2000 System "Instructions For Use." 15 pages (2017).
Verhelse et al., "Cloning of 16S rRNA genes amplified from normal and disturbed vaginal microflora suggests a strong association between Atopobium vaginae, Gardnerella vaginalis and bacterial vaginosis." BMC Microbiology, 4(1): 1471-2180 (2004).
Wei et al. "Up-regulation of NICE-3 as a Novel EDC Gene Could Contribute to Human Hepatocellular Carcinoma." Asian Pacific Journal of Cancer Prevention, 13(9): 4363-4368 (2012).

* cited by examiner

*Primary Examiner* — Aaron A Priest
(74) *Attorney, Agent, or Firm* — Adam M. Breier; Jeffrey E. Landes

(57) ABSTRACT

This disclosure provides oligomers, combinations of oligomers, compositions, kits, uses, and methods for detecting a C1orf43 nucleic acid, such as C1orf43 mRNA, such as human C1orf43 mRNA, in a sample.

21 Claims, No Drawings

Specification includes a Sequence Listing.

SEQUENCE LISTING

<160> NUMBER OF SEQ ID NOS: 72

<210> SEQ ID NO 1
<211> LENGTH: 1802
<212> TYPE: DNA
<213> ORGANISM: Homo sapiens

<400> SEQUENCE: 1

| | | | | | |
|---|---|---|---|---|---|
| gtgcgcgtgc | cgcctcgcca | cgagacacct | ctttccggct | ccgcgagtcc | accccgcctc | 60 |
| cttcacggcg | gccctgcctc | caccacgtga | cgcacggatg | gccgccgctt | cctcttactg | 120 |
| tcgtagttcc | gcgtctgagc | gctcgacgct | cctgggtgcc | attgcctgcc | tgagtcacgt | 180 |
| gtcaggggga | agctggaagg | cgtcgttctc | ctttcccagc | tctcctgcct | gtccgccatg | 240 |
| ttttcaggcc | gggtctggct | tggtcttccc | ccgtaaggaa | atggccgggg | agctccaggg | 300 |
| gacccaggcg | ccgtcgcttc | ggcggagcct | gggctgacca | gccaggacag | cggggtaaac | 360 |
| ccgaacaatt | ctgcgcgagg | tagggaggcc | atggcgtccg | gcagtaactg | gctctccggg | 420 |
| gtgaatgtcg | tgctggtgat | ggcctacggg | agcctggact | tgaaagagga | gattgatatt | 480 |
| cgactctcca | gggttcagga | tatcaagtat | gagccccagc | tccttgcaga | tgatgatgct | 540 |
| agactactac | aactggaaac | ccagggaaat | caaagttgct | acaactatct | gtataggatg | 600 |
| aaagctctgg | atgccattcg | tacctctgag | atcccatttc | attctgaagg | ccggcatccc | 660 |
| cgttccttaa | tgggcaagaa | tttccgctcc | tacctgctgg | atctgcgaaa | cactagtacg | 720 |
| cctttcaagg | gtgtacgcaa | agcactcatt | gataccctt | tggatggcta | tgaaacagcc | 780 |
| cgctatggga | caggggtctt | tggccagaat | gagtacctac | gctatcagga | ggccctgagt | 840 |
| gagctggcca | ctgcggttaa | agcacgaatt | gggagctctc | agcgacatca | ccagtcagca | 900 |
| gccaaagacc | taactcagtc | cctgaggtc | tccccaacaa | ccatccaggt | gacataccc | 960 |
| ccctccagtc | agaagagtaa | acgtgccaag | cacttccttg | aattgaagag | ctttaaggat | 1020 |
| aactataaca | cattggagag | tactctgtga | cggagctgaa | ggactcttgc | cgtagattaa | 1080 |
| gccagtcagt | tgcaatgtgc | aagacaggct | gcttgccggg | ccgccctcgg | aacatctggc | 1140 |
| ccagcaggcc | cagactgtat | ccatccaagt | tcccgttgta | tccagagttc | ttagagcttg | 1200 |
| tgtctaaagg | gtaattcccc | aacccttcct | tatgagcatt | tttagaacat | tggctaagac | 1260 |
| tattttcccc | cagtagcgct | tttttctgga | tttgcattca | ggtgttattc | ttaatgtttc | 1320 |
| tgtcaaagct | tcttaaaaat | cttcacttgg | tttcagccat | agttcacctt | ccctgttcca | 1380 |
| ggtttattta | attccaaagg | tgagagttgg | agtgagatgt | cttccatatc | tatacctttg | 1440 |
| tgcacagttg | aatgggaact | gtttgggttt | agggcatctt | agagttgatt | gatggaaaaa | 1500 |
| gcagacagga | actggtggga | ggtcaagtgg | ggaagttggt | gaatgtggaa | taacttacct | 1560 |
| ttgtgctcca | cttaaaccag | atgtgttgca | gctttcctga | catgcaagga | tctactttaa | 1620 |
| ttccacactc | tcattaataa | attgaataaa | agggaatgtt | ttggcacctg | atataatctg | 1680 |
| ccaggctatg | tgacagtagg | aaggaatggt | ttcccctaac | aagcccaatg | cactggtctg | 1740 |
| actttataaa | ttatttaata | aaatgaacta | ttatcaaata | aaacgtatga | atcagtcctt | 1800 |
| ta | | | | | | 1802 |

<210> SEQ ID NO 2

<400> SEQUENCE: 2

000

<210> SEQ ID NO 3
<211> LENGTH: 1012
<212> TYPE: DNA
<213> ORGANISM: Artificial Sequence
<220> FEATURE:
<223> OTHER INFORMATION: Construct for in vitro transcription
<220> FEATURE:
<221> NAME/KEY: MISC_FEATURE
<222> LOCATION: (17)..(36)
<223> OTHER INFORMATION: T7 promoter

<400> SEQUENCE: 3

```
cgacgaagac tctctttaat acgactcact atagggaagc ttgtgcgcgt gccgcctcgc      60
cacgagacac ctctttccgg ctccgcgagt ccaccccgcc tccttcacgg cggccctgcc    120
tccaccacgt gacgcacgga tggccgccgc ttcctcttac tgtcgtagtt ccgcgtctga    180
gcgctcgacg ctcctgggtg ccattgcctg cctgagtcac gtgtcagggg gaagctggaa    240
ggcgtcgttc tccttttccca gctctcctgc ctgtccgcca tgttttcagg ccgggtctgg    300
cttggtcttc ccccgtaagg aaatggccgg ggagctccag gggacccagg cgccgtcgct    360
tcggcggagc ctgggctgac cagccaggac agcggggtaa acccgaacaa ttctgcgcga    420
ggtagggagg ccatggcgtc cggcagtaac tggctctccg gggtgaatgt cgtgctggtg    480
atggcctacg ggagcctgga cttgaaagag gagattgata ttcgactctc cagggttcag    540
gatatcaagt atgagcccca gctccttgca gatgatgatg ctagactact acaactggaa    600
acccagggaa atcaaagttg ctacaactat ctgtatagga tgaaagctct ggatgccatt    660
cgtacctctg agatcccatt tcattctgaa ggccggcatc cccgttcctt aatgggcaag    720
aatttccgct cctacctgct ggatctgcga aacactagta cgcctttcaa gggtgtacgc    780
aaagcactca ttgataccct tttggatggc tatgaaacag cccgctatgg gacaggggtc    840
tttggccaga atgagtacct acgctatcag gaggccctga gtgagctggc cactgcggtt    900
aaagcacgaa ttgggagctc tcagcgacat caccagtcag cagccaaaga cctaactcag    960
tccccctgagg tctccccaac aaccatcgcg gccgcgtcca tccaacacat gc          1012
```

<210> SEQ ID NO 4
<211> LENGTH: 58
<212> TYPE: DNA
<213> ORGANISM: Artificial Sequence
<220> FEATURE:
<223> OTHER INFORMATION: Capture oligomer

<400> SEQUENCE: 4

```
ccaaacagtt cccattcaac tgtgctttaa aaaaaaaaa aaaaaaaaa aaaaaaa          58
```

<210> SEQ ID NO 5
<211> LENGTH: 25
<212> TYPE: DNA
<213> ORGANISM: Artificial Sequence
<220> FEATURE:
<223> OTHER INFORMATION: Capture oligomer THS

<400> SEQUENCE: 5

```
ccaaacagtt cccattcaac tgtgc                                            25
```

<210> SEQ ID NO 6
<211> LENGTH: 60
<212> TYPE: DNA
<213> ORGANISM: Artificial Sequence
<220> FEATURE:
<223> OTHER INFORMATION: Capture oligomer

```
<220> FEATURE:
<221> NAME/KEY: misc_feature
<222> LOCATION: (1)..(60)
<223> OTHER INFORMATION: N = U

<400> SEQUENCE: 6
caaaggnana gananggaag acancncttt aaaaaaaaaa aaaaaaaaaa aaaaaaaaaa         60

<210> SEQ ID NO 7
<211> LENGTH: 27
<212> TYPE: DNA
<213> ORGANISM: Artificial Sequence
<220> FEATURE:
<223> OTHER INFORMATION: Capture oligomer THS
<220> FEATURE:
<221> NAME/KEY: misc_feature
<222> LOCATION: (1)..(27)
<223> OTHER INFORMATION: N = U

<400> SEQUENCE: 7
caaaggnana gananggaag acancnc                                            27

<210> SEQ ID NO 8
<211> LENGTH: 57
<212> TYPE: DNA
<213> ORGANISM: Artificial Sequence
<220> FEATURE:
<223> OTHER INFORMATION: Capture oligomer
<220> FEATURE:
<221> NAME/KEY: misc_feature
<222> LOCATION: (1)..(57)
<223> OTHER INFORMATION: N = U

<400> SEQUENCE: 8
cngngcacaa aggnanagan anggtttaaa aaaaaaaaaa aaaaaaaaaa aaaaaaa           57

<210> SEQ ID NO 9
<211> LENGTH: 24
<212> TYPE: DNA
<213> ORGANISM: Artificial Sequence
<220> FEATURE:
<223> OTHER INFORMATION: Capture oligomer THS
<220> FEATURE:
<221> NAME/KEY: misc_feature
<222> LOCATION: (1)..(24)
<223> OTHER INFORMATION: N = U

<400> SEQUENCE: 9
cngngcacaa aggnanagan angg                                               24

<210> SEQ ID NO 10
<211> LENGTH: 58
<212> TYPE: DNA
<213> ORGANISM: Artificial Sequence
<220> FEATURE:
<223> OTHER INFORMATION: Capture oligomer
<220> FEATURE:
<221> NAME/KEY: misc_feature
<222> LOCATION: (1)..(58)
<223> OTHER INFORMATION: N = U

<400> SEQUENCE: 10
canncaacng ngcacaaagg nanagtttaa aaaaaaaaaa aaaaaaaaaa aaaaaaaa          58

<210> SEQ ID NO 11
<211> LENGTH: 25
<212> TYPE: DNA
<213> ORGANISM: Artificial Sequence
<220> FEATURE:
```

```
<223> OTHER INFORMATION: Capture oligomer THS
<220> FEATURE:
<221> NAME/KEY: misc_feature
<222> LOCATION: (1)..(25)
<223> OTHER INFORMATION: N = U

<400> SEQUENCE: 11
canncaacng ngcacaaagg nanag                                          25

<210> SEQ ID NO 12
<211> LENGTH: 58
<212> TYPE: DNA
<213> ORGANISM: Artificial Sequence
<220> FEATURE:
<223> OTHER INFORMATION: Capture oligomer
<220> FEATURE:
<221> NAME/KEY: misc_feature
<222> LOCATION: (1)..(58)
<223> OTHER INFORMATION: N = U

<400> SEQUENCE: 12
ccaaacagnn cccanncaac ngngctttaa aaaaaaaaaa aaaaaaaaaa aaaaaaaa      58

<210> SEQ ID NO 13
<211> LENGTH: 25
<212> TYPE: DNA
<213> ORGANISM: Artificial Sequence
<220> FEATURE:
<223> OTHER INFORMATION: Capture oligomer THS
<220> FEATURE:
<221> NAME/KEY: misc_feature
<222> LOCATION: (1)..(25)
<223> OTHER INFORMATION: N = U

<400> SEQUENCE: 13
ccaaacagnn cccanncaac ngngc                                         25

<210> SEQ ID NO 14
<211> LENGTH: 26
<212> TYPE: DNA
<213> ORGANISM: Artificial Sequence
<220> FEATURE:
<223> OTHER INFORMATION: C1orf43 molecular torch. 5F3D.
<220> FEATURE:
<221> NAME/KEY: misc_feature
<222> LOCATION: (1)..(20)
<223> OTHER INFORMATION: N = U
<220> FEATURE:
<221> NAME/KEY: misc_feature
<222> LOCATION: (23)..(24)
<223> OTHER INFORMATION: N = 2'-O-methylated C
<220> FEATURE:
<221> NAME/KEY: misc_feature
<222> LOCATION: (25)..(25)
<223> OTHER INFORMATION: N = 2'-O-methylated A
<220> FEATURE:
<221> NAME/KEY: misc_feature
<222> LOCATION: (26)..(26)
<223> OTHER INFORMATION: N = 2'-O-methylated C

<400> SEQUENCE: 14
gnggaanaac nnaccnnngn gcnnnn                                        26

<210> SEQ ID NO 15
<211> LENGTH: 22
<212> TYPE: DNA
<213> ORGANISM: Artificial Sequence
<220> FEATURE:
<223> OTHER INFORMATION: C1orf43 detection oligomer THS
<220> FEATURE:
<221> NAME/KEY: misc_feature
```

-continued

```
<222> LOCATION: (1)..(22)
<223> OTHER INFORMATION: N = U

<400> SEQUENCE: 15
gnggaanaac nnaccnnngn gc                                           22

<210> SEQ ID NO 16
<211> LENGTH: 25
<212> TYPE: DNA
<213> ORGANISM: Artificial Sequence
<220> FEATURE:
<223> OTHER INFORMATION: C1orf43 molecular torch. 21-C9. 5F3D.
<220> FEATURE:
<221> NAME/KEY: misc_feature
<222> LOCATION: (1)..(20)
<223> OTHER INFORMATION: N = U
<220> FEATURE:
<221> NAME/KEY: misc_feature
<222> LOCATION: (21)..(22)
<223> OTHER INFORMATION: (CH2)9-linker follows position 21
<220> FEATURE:
<221> NAME/KEY: misc_feature
<222> LOCATION: (22)..(22)
<223> OTHER INFORMATION: N = 2'-O-methylated G
<220> FEATURE:
<221> NAME/KEY: misc_feature
<222> LOCATION: (23)..(23)
<223> OTHER INFORMATION: N = 2'-O-methylated A
<220> FEATURE:
<221> NAME/KEY: misc_feature
<222> LOCATION: (24)..(25)
<223> OTHER INFORMATION: N = 2'-O-methylated C

<400> SEQUENCE: 16
ggncaagngg ggaagnnggn gnnnn                                        25

<210> SEQ ID NO 17
<211> LENGTH: 21
<212> TYPE: DNA
<213> ORGANISM: Artificial Sequence
<220> FEATURE:
<223> OTHER INFORMATION: C1orf43 detection oligomer THS
<220> FEATURE:
<221> NAME/KEY: misc_feature
<222> LOCATION: (1)..(21)
<223> OTHER INFORMATION: N = U

<400> SEQUENCE: 17
ggncaagngg ggaagnnggn g                                            21

<210> SEQ ID NO 18
<211> LENGTH: 23
<212> TYPE: DNA
<213> ORGANISM: Artificial Sequence
<220> FEATURE:
<223> OTHER INFORMATION: C1orf43 molecular torch. 19-C9. 5F3D.
<220> FEATURE:
<221> NAME/KEY: misc_feature
<222> LOCATION: (1)..(17)
<223> OTHER INFORMATION: N = U
<220> FEATURE:
<221> NAME/KEY: misc_feature
<222> LOCATION: (19)..(20)
<223> OTHER INFORMATION: (CH2)9-linker follows position 19
<220> FEATURE:
<221> NAME/KEY: misc_feature
<222> LOCATION: (20)..(20)
<223> OTHER INFORMATION: N = 2'-O-methylated U
<220> FEATURE:
<221> NAME/KEY: misc_feature
<222> LOCATION: (21)..(23)
<223> OTHER INFORMATION: N = 2'-O-methylated C
```

<400> SEQUENCE: 18
gggaagnngg ngaangnggn nnn                              23

<210> SEQ ID NO 19
<211> LENGTH: 19
<212> TYPE: DNA
<213> ORGANISM: Artificial Sequence
<220> FEATURE:
<223> OTHER INFORMATION: C1orf43 detection oligomer THS
<220> FEATURE:
<221> NAME/KEY: misc_feature
<222> LOCATION: (1)..(19)
<223> OTHER INFORMATION: N = U

<400> SEQUENCE: 19
gggaagnngg ngaangngg                                   19

<210> SEQ ID NO 20
<211> LENGTH: 26
<212> TYPE: DNA
<213> ORGANISM: Artificial Sequence
<220> FEATURE:
<223> OTHER INFORMATION: C1orf43 molecular torch. 5F3D.
<220> FEATURE:
<221> NAME/KEY: misc_feature
<222> LOCATION: (1)..(19)
<223> OTHER INFORMATION: N = U
<220> FEATURE:
<221> NAME/KEY: misc_feature
<222> LOCATION: (23)..(23)
<223> OTHER INFORMATION: N = 2'-O-methylated C
<220> FEATURE:
<221> NAME/KEY: misc_feature
<222> LOCATION: (24)..(24)
<223> OTHER INFORMATION: N = 2'-O-methylated A
<220> FEATURE:
<221> NAME/KEY: misc_feature
<222> LOCATION: (25)..(26)
<223> OTHER INFORMATION: N = 2'-O-methylated A

<400> SEQUENCE: 20
ggngaangng gaanaacnna ccnnnn                           26

<210> SEQ ID NO 21
<211> LENGTH: 22
<212> TYPE: DNA
<213> ORGANISM: Artificial Sequence
<220> FEATURE:
<223> OTHER INFORMATION: C1orf43 detection oligomer THS
<220> FEATURE:
<221> NAME/KEY: misc_feature
<222> LOCATION: (1)..(22)
<223> OTHER INFORMATION: N = U

<400> SEQUENCE: 21
ggngaangng gaanaacnna cc                               22

<210> SEQ ID NO 22
<211> LENGTH: 32
<212> TYPE: DNA
<213> ORGANISM: Artificial Sequence
<220> FEATURE:
<223> OTHER INFORMATION: C1orf43 molecular beacon. 5F3D.
<220> FEATURE:
<221> NAME/KEY: misc_feature
<222> LOCATION: (1)..(2)
<223> OTHER INFORMATION: N = 2'-O-methylated G
<220> FEATURE:
<221> NAME/KEY: misc_feature
<222> LOCATION: (3)..(3)
<223> OTHER INFORMATION: N = 2'-O-methylated C

```
<220> FEATURE:
<221> NAME/KEY: misc_feature
<222> LOCATION: (4)..(4)
<223> OTHER INFORMATION: N = 2'-O-methylated U
<220> FEATURE:
<221> NAME/KEY: misc_feature
<222> LOCATION: (5)..(5)
<223> OTHER INFORMATION: N = 2'-O-methylated C
<220> FEATURE:
<221> NAME/KEY: misc_feature
<222> LOCATION: (6)..(25)
<223> OTHER INFORMATION: N = U
<220> FEATURE:
<221> NAME/KEY: misc_feature
<222> LOCATION: (28)..(28)
<223> OTHER INFORMATION: N = 2'-O-methylated G
<220> FEATURE:
<221> NAME/KEY: misc_feature
<222> LOCATION: (29)..(29)
<223> OTHER INFORMATION: N = 2'-O-methylated A
<220> FEATURE:
<221> NAME/KEY: misc_feature
<222> LOCATION: (30)..(30)
<223> OTHER INFORMATION: N = 2'-O-methylated A
<220> FEATURE:
<221> NAME/KEY: misc_feature
<222> LOCATION: (31)..(32)
<223> OTHER INFORMATION: N = 2'-O-methylated C

<400> SEQUENCE: 22
nnnnngngga anaacnnacc nnngngcnnn nn                                    32

<210> SEQ ID NO 23
<211> LENGTH: 22
<212> TYPE: DNA
<213> ORGANISM: Artificial Sequence
<220> FEATURE:
<223> OTHER INFORMATION: C1orf43 detection oligomer THS
<220> FEATURE:
<221> NAME/KEY: misc_feature
<222> LOCATION: (1)..(22)
<223> OTHER INFORMATION: N = U

<400> SEQUENCE: 23
gnggaanaac nnaccnnngn gc                                               22

<210> SEQ ID NO 24
<211> LENGTH: 32
<212> TYPE: DNA
<213> ORGANISM: Artificial Sequence
<220> FEATURE:
<223> OTHER INFORMATION: C1orf43 molecular beacon. 5F3D.
<220> FEATURE:
<221> NAME/KEY: misc_feature
<222> LOCATION: (1)..(2)
<223> OTHER INFORMATION: N = 2'-O-methylated G
<220> FEATURE:
<221> NAME/KEY: misc_feature
<222> LOCATION: (3)..(3)
<223> OTHER INFORMATION: N = 2'-O-methylated C
<220> FEATURE:
<221> NAME/KEY: misc_feature
<222> LOCATION: (4)..(4)
<223> OTHER INFORMATION: N = 2'-O-methylated U
<220> FEATURE:
<221> NAME/KEY: misc_feature
<222> LOCATION: (5)..(5)
<223> OTHER INFORMATION: N = 2'-O-methylated C
<220> FEATURE:
<221> NAME/KEY: misc_feature
<222> LOCATION: (6)..(27)
<223> OTHER INFORMATION: N = U
<220> FEATURE:
<221> NAME/KEY: misc_feature
<222> LOCATION: (28)..(28)
```

<223> OTHER INFORMATION: N = 2'-O-methylated G
<220> FEATURE:
<221> NAME/KEY: misc_feature
<222> LOCATION: (29)..(29)
<223> OTHER INFORMATION: N = 2'-O-methylated A
<220> FEATURE:
<221> NAME/KEY: misc_feature
<222> LOCATION: (30)..(30)
<223> OTHER INFORMATION: N = 2'-O-methylated G
<220> FEATURE:
<221> NAME/KEY: misc_feature
<222> LOCATION: (31)..(32)
<223> OTHER INFORMATION: N = 2'-O-methylated C

<400> SEQUENCE: 24
ggcncggnga angnggaana acnnaccnnn nn           32

<210> SEQ ID NO 25
<211> LENGTH: 22
<212> TYPE: DNA
<213> ORGANISM: Artificial Sequence
<220> FEATURE:
<223> OTHER INFORMATION: C1orf43 detection oligomer THS
<220> FEATURE:
<221> NAME/KEY: misc_feature
<222> LOCATION: (1)..(22)
<223> OTHER INFORMATION: N = U

<400> SEQUENCE: 25
ggngaangng gaanaacnna cc           22

<210> SEQ ID NO 26
<211> LENGTH: 55
<212> TYPE: DNA
<213> ORGANISM: Artificial Sequence
<220> FEATURE:
<223> OTHER INFORMATION: C1orf43 promoter primer

<400> SEQUENCE: 26
aatttaatac gactcactat agggagagca tgtcaggaaa gctgcaacac atctg           55

<210> SEQ ID NO 27
<211> LENGTH: 28
<212> TYPE: DNA
<213> ORGANISM: Artificial Sequence
<220> FEATURE:
<223> OTHER INFORMATION: C1orf43 amplification oligomer or amplification
      oligomer THS

<400> SEQUENCE: 27
gcatgtcagg aaagctgcaa cacatctg           28

<210> SEQ ID NO 28
<211> LENGTH: 55
<212> TYPE: DNA
<213> ORGANISM: Artificial Sequence
<220> FEATURE:
<223> OTHER INFORMATION: C1orf43 promoter primer

<400> SEQUENCE: 28
aatttaatac gactcactat agggagagct gcaacacatc tggtttaagt ggagc           55

<210> SEQ ID NO 29
<211> LENGTH: 28
<212> TYPE: DNA
<213> ORGANISM: Artificial Sequence
<220> FEATURE:
<223> OTHER INFORMATION: C1orf43 amplification oligomer or amplification
      oligomer THS

<400> SEQUENCE: 29
gctgcaacac atctggttta agtggagc                                   28

<210> SEQ ID NO 30
<211> LENGTH: 54
<212> TYPE: DNA
<213> ORGANISM: Artificial Sequence
<220> FEATURE:
<223> OTHER INFORMATION: C1orf43 promoter primer

<400> SEQUENCE: 30
aatttaatac gactcactat agggagagga aagctgcaac acatctggtt taag       54

<210> SEQ ID NO 31
<211> LENGTH: 27
<212> TYPE: DNA
<213> ORGANISM: Artificial Sequence
<220> FEATURE:
<223> OTHER INFORMATION: C1orf43 amplification oligomer or amplification
      oligomer THS

<400> SEQUENCE: 31
ggaaagctgc aacacatctg gtttaag                                     27

<210> SEQ ID NO 32
<211> LENGTH: 55
<212> TYPE: DNA
<213> ORGANISM: Artificial Sequence
<220> FEATURE:
<223> OTHER INFORMATION: C1orf43 promoter primer

<400> SEQUENCE: 32
aatttaatac gactcactat agggagagta gatccttgca tgtcaggaaa gctgc      55

<210> SEQ ID NO 33
<211> LENGTH: 28
<212> TYPE: DNA
<213> ORGANISM: Artificial Sequence
<220> FEATURE:
<223> OTHER INFORMATION: C1orf43 amplification oligomer or amplification
      oligomer THS

<400> SEQUENCE: 33
gtagatcctt gcatgtcagg aaagctgc                                    28

<210> SEQ ID NO 34
<211> LENGTH: 21
<212> TYPE: DNA
<213> ORGANISM: Artificial Sequence
<220> FEATURE:
<223> OTHER INFORMATION: C1orf43 amplification oligomer or amplification
      oligomer THS

<400> SEQUENCE: 34
gcagacagga actggtggga g                                           21

<210> SEQ ID NO 35
<211> LENGTH: 23
<212> TYPE: DNA
<213> ORGANISM: Artificial Sequence
<220> FEATURE:
<223> OTHER INFORMATION: C1orf43 amplification oligomer or amplification
      oligomer THS

<400> SEQUENCE: 35
ggcatcttag agttgattga tgg                                       23

<210> SEQ ID NO 36
<211> LENGTH: 25
<212> TYPE: DNA
<213> ORGANISM: Artificial Sequence
<220> FEATURE:
<223> OTHER INFORMATION: C1orf43 amplification oligomer or amplification
      oligomer THS

<400> SEQUENCE: 36
cttagagttg attgatggaa aaagc                                     25

<210> SEQ ID NO 37
<211> LENGTH: 21
<212> TYPE: DNA
<213> ORGANISM: Artificial Sequence
<220> FEATURE:
<223> OTHER INFORMATION: C1orf43 amplification oligomer or amplification
      oligomer THS

<400> SEQUENCE: 37
ggaaaaagca gacaggaact g                                         21

<210> SEQ ID NO 38
<211> LENGTH: 18
<212> TYPE: DNA
<213> ORGANISM: Artificial Sequence
<220> FEATURE:
<223> OTHER INFORMATION: C1orf43 amplification oligomer or amplification
      oligomer THS

<400> SEQUENCE: 38
gcagacagga actggtgg                                             18

<210> SEQ ID NO 39
<211> LENGTH: 202
<212> TYPE: DNA
<213> ORGANISM: Artificial Sequence
<220> FEATURE:
<223> OTHER INFORMATION: C1orf43 region encompassing exemplary amplicons

<400> SEQUENCE: 39
gagatgtctt ccatatctat acctttgtgc acagttgaat gggaactgtt tgggtttagg    60
gcatcttaga gttgattgat ggaaaaagca gacaggaact ggtgggaggt caagtgggga   120
agttggtgaa tgtggaataa cttacctttg tgctccactt aaaccagatg tgttgcagct   180
ttcctgacat gcaaggatct ac                                          202

<210> SEQ ID NO 40
<211> LENGTH: 143
<212> TYPE: DNA
<213> ORGANISM: Artificial Sequence
<220> FEATURE:
<223> OTHER INFORMATION: Exemplary C1orf43 amplification product

<400> SEQUENCE: 40
ggcatcttag agttgattga tggaaaaagc agacaggaac tggtgggagg tcaagtgggg    60
aagttggtga atgtggaata acttaccttt gtgctccact taaaccagat gtgttgcagc   120
tttcctgaca tgcaaggatc tac                                         143

<210> SEQ ID NO 41
<211> LENGTH: 105
<212> TYPE: DNA

```
<213> ORGANISM: Artificial Sequence
<220> FEATURE:
<223> OTHER INFORMATION: Exemplary C1orf43 amplification product

<400> SEQUENCE: 41
gcagacagga actggtggga ggtcaagtgg ggaagttggt gaatgtggaa taacttacct      60
ttgtgctcca cttaaaccag atgtgttgca gctttcctga catgc                    105

<210> SEQ ID NO 42
<211> LENGTH: 92
<212> TYPE: DNA
<213> ORGANISM: Artificial Sequence
<220> FEATURE:
<223> OTHER INFORMATION: Exemplary C1orf43 amplification product

<400> SEQUENCE: 42
gcagacagga actggtggga ggtcaagtgg ggaagttggt gaatgtggaa taacttacct      60
ttgtgctcca cttaaaccag atgtgttgca gc                                   92

<210> SEQ ID NO 43
<211> LENGTH: 92
<212> TYPE: DNA
<213> ORGANISM: Artificial Sequence
<220> FEATURE:
<223> OTHER INFORMATION: C1orf43 region encompassing exemplary detection
      oligomer
      hybridization sites

<400> SEQUENCE: 43
aaaaagcaga caggaactgg tgggaggtca agtggggaag ttggtgaatg tggaataact      60
tacctttgtg ctccacttaa accagatgtg tt                                   92

<210> SEQ ID NO 44
<211> LENGTH: 55
<212> TYPE: DNA
<213> ORGANISM: Artificial Sequence
<220> FEATURE:
<223> OTHER INFORMATION: C1orf43 region encompassing exemplary detection
      oligomer
      hybridization sites

<400> SEQUENCE: 44
tcaagtgggg aagttggtga atgtggaata acttaccttt gtgctccact taaac           55

<210> SEQ ID NO 45
<211> LENGTH: 43
<212> TYPE: DNA
<213> ORGANISM: Artificial Sequence
<220> FEATURE:
<223> OTHER INFORMATION: C1orf43 region encompassing exemplary detection
      oligomer
      hybridization sites

<400> SEQUENCE: 45
gtcaagtggg gaagttggtg aatgtggaat aacttacctt tgt                        43

<210> SEQ ID NO 46
<211> LENGTH: 49
<212> TYPE: DNA
<213> ORGANISM: Artificial Sequence
<220> FEATURE:
<223> OTHER INFORMATION: C1orf43 region encompassing exemplary
      amplification oligomer (e.g., nonT7) hybridization sites

<400> SEQUENCE: 46
```
ggcatcttag agttgattga tggaaaaagc agacaggaac tggtgggag         49

<210> SEQ ID NO 47
<211> LENGTH: 14
<212> TYPE: DNA
<213> ORGANISM: Artificial Sequence
<220> FEATURE:
<223> OTHER INFORMATION: exemplary amplification oligomer (e.g., nonT7)
      core sequence

<400> SEQUENCE: 47
gcagacagga actg         14

<210> SEQ ID NO 48
<211> LENGTH: 18
<212> TYPE: DNA
<213> ORGANISM: Artificial Sequence
<220> FEATURE:
<223> OTHER INFORMATION: exemplary amplification oligomer (e.g., nonT7)
      core sequence

<400> SEQUENCE: 48
cttagagttg attgatgg         18

<210> SEQ ID NO 49
<211> LENGTH: 46
<212> TYPE: DNA
<213> ORGANISM: Artificial Sequence
<220> FEATURE:
<223> OTHER INFORMATION: C1orf43 region encompassing exemplary detection
      oligomer hybridization sites
<220> FEATURE:
<221> NAME/KEY: misc_feature
<222> LOCATION: (1)..(46)
<223> OTHER INFORMATION: N = U

<400> SEQUENCE: 49
ggncaagngg ggaagnnggn gaangnggaa naacnnaccn nngngc         46

<210> SEQ ID NO 50
<211> LENGTH: 15
<212> TYPE: DNA
<213> ORGANISM: Artificial Sequence
<220> FEATURE:
<223> OTHER INFORMATION: exemplary detection oligomer core seqeunce
<220> FEATURE:
<221> NAME/KEY: misc_feature
<222> LOCATION: (1)..(15)
<223> OTHER INFORMATION: N = U

<400> SEQUENCE: 50
gnggaanaac nnacc         15

<210> SEQ ID NO 51
<211> LENGTH: 13
<212> TYPE: DNA
<213> ORGANISM: Artificial Sequence
<220> FEATURE:
<223> OTHER INFORMATION: exemplary detection oligomer core seqeunce
<220> FEATURE:
<221> NAME/KEY: misc_feature
<222> LOCATION: (1)..(13)
<223> OTHER INFORMATION: N = U

<400> SEQUENCE: 51
ggggaagnng gng         13

<210> SEQ ID NO 52

```
<211> LENGTH: 51
<212> TYPE: DNA
<213> ORGANISM: Artificial Sequence
<220> FEATURE:
<223> OTHER INFORMATION: C1orf43 region encompassing exemplary
      amplification oligomer (e.g., promoter primer) hybridization sites
<220> FEATURE:
<221> NAME/KEY: misc-feature
<222> LOCATION: (1)..(51)
<223> OTHER INFORMATION: N = U

<400> SEQUENCE: 52
gtagatcctt gcatgtcagg aaagctgcaa cacatctggt ttaagtggag c            51

<210> SEQ ID NO 53
<211> LENGTH: 15
<212> TYPE: DNA
<213> ORGANISM: Artificial Sequence
<220> FEATURE:
<223> OTHER INFORMATION: Exemplary amplification oligomer (e.g.,
      promoter primer) core sequence

<400> SEQUENCE: 53
gctgcaacac atctg                                                    15

<210> SEQ ID NO 54
<211> LENGTH: 10
<212> TYPE: DNA
<213> ORGANISM: Artificial Sequence
<220> FEATURE:
<223> OTHER INFORMATION: Exemplary amplification oligomer (e.g.,
      promoter primer) core sequence

<400> SEQUENCE: 54
ggaaagctgc                                                          10

<210> SEQ ID NO 55
<211> LENGTH: 53
<212> TYPE: DNA
<213> ORGANISM: Artificial Sequence
<220> FEATURE:
<223> OTHER INFORMATION: C1orf43 region encompassing exemplary capture
      oligomer hybridization sites
<220> FEATURE:
<221> NAME/KEY: misc_feature
<222> LOCATION: (1)..(53)
<223> OTHER INFORMATION: N = U

<400> SEQUENCE: 55
ccaaacagnn cccanncaac ngngcacaaa ggnanagana nggaagacan cnc          53

<210> SEQ ID NO 56
<211> LENGTH: 11
<212> TYPE: DNA
<213> ORGANISM: Artificial Sequence
<220> FEATURE:
<223> OTHER INFORMATION: Exemplary capture oligomer core sequence
<220> FEATURE:
<221> NAME/KEY: misc_feature
<222> LOCATION: (1)..(11)
<223> OTHER INFORMATION: N = U

<400> SEQUENCE: 56
caaaggnana g                                                        11

<210> SEQ ID NO 57
<211> LENGTH: 13
<212> TYPE: DNA
<213> ORGANISM: Artificial Sequence
```

```
<220> FEATURE:
<223> OTHER INFORMATION: Exemplary capture oligomer core sequence
<220> FEATURE:
<221> NAME/KEY: misc_feature
<222> LOCATION: (1)..(13)
<223> OTHER INFORMATION: N = U

<400> SEQUENCE: 57
canncaacng ngc                                                            13

<210> SEQ ID NO 58
<211> LENGTH: 27
<212> TYPE: DNA
<213> ORGANISM: Artificial Sequence
<220> FEATURE:
<223> OTHER INFORMATION: Exemplary T7 promoter sequence
<220> FEATURE:
<221> NAME/KEY: misc_feature
<222> LOCATION: (1)..(27)
<223> OTHER INFORMATION: N = U

<400> SEQUENCE: 58
aatttaatac gactcactat agggaga                                             27

<210> SEQ ID NO 59
<211> LENGTH: 20
<212> TYPE: DNA
<213> ORGANISM: Artificial Sequence
<220> FEATURE:
<223> OTHER INFORMATION: C1orf43 linear detection probe
<220> FEATURE:
<221> NAME/KEY: misc_feature
<222> LOCATION: (1)..(20)
<223> OTHER INFORMATION: N = U

<400> SEQUENCE: 59
gngaangngg aanaacnnac                                                     20

<210> SEQ ID NO 60
<211> LENGTH: 15
<212> TYPE: DNA
<213> ORGANISM: Artificial Sequence
<220> FEATURE:
<223> OTHER INFORMATION: C1orf43 linear detection probe
<220> FEATURE:
<221> NAME/KEY: misc_feature
<222> LOCATION: (1)..(15)
<223> OTHER INFORMATION: N = U

<400> SEQUENCE: 60
gnggggaagn nggng                                                          15

<210> SEQ ID NO 61
<211> LENGTH: 19
<212> TYPE: DNA
<213> ORGANISM: Artificial Sequence
<220> FEATURE:
<223> OTHER INFORMATION: C1orf43 linear detection probe
<220> FEATURE:
<221> NAME/KEY: misc_feature
<222> LOCATION: (1)..(19)
<223> OTHER INFORMATION: N = U

<400> SEQUENCE: 61
caccnnanng aanggaaac                                                      19

<210> SEQ ID NO 62
<211> LENGTH: 17
<212> TYPE: DNA
```

```
<213> ORGANISM: Artificial Sequence
<220> FEATURE:
<223> OTHER INFORMATION: C1orf43 linear detection probe
<220> FEATURE:
<221> NAME/KEY: misc_feature
<222> LOCATION: (1)..(17)
<223> OTHER INFORMATION: N = U

<400> SEQUENCE: 62
cnncaaccac nnacacc                                                    17

<210> SEQ ID NO 63
<211> LENGTH: 19
<212> TYPE: DNA
<213> ORGANISM: Artificial Sequence
<220> FEATURE:
<223> OTHER INFORMATION: C1orf43 linear detection probe
<220> FEATURE:
<221> NAME/KEY: misc_feature
<222> LOCATION: (1)..(19)
<223> OTHER INFORMATION: N = U

<400> SEQUENCE: 63
cnnacaccnn anngaangg                                                  19

<210> SEQ ID NO 64
<211> LENGTH: 18
<212> TYPE: DNA
<213> ORGANISM: Artificial Sequence
<220> FEATURE:
<223> OTHER INFORMATION: C1orf43 linear detection probe
<220> FEATURE:
<221> NAME/KEY: misc_feature
<222> LOCATION: (1)..(18)
<223> OTHER INFORMATION: N = U

<400> SEQUENCE: 64
gaanaacnna ccnnngng                                                   18

<210> SEQ ID NO 65
<211> LENGTH: 20
<212> TYPE: DNA
<213> ORGANISM: Artificial Sequence
<220> FEATURE:
<223> OTHER INFORMATION: C1orf43 linear detection probe
<220> FEATURE:
<221> NAME/KEY: misc_feature
<222> LOCATION: (1)..(20)
<223> OTHER INFORMATION: N = U

<400> SEQUENCE: 65
caaccacnna caccnnanng                                                 20

<210> SEQ ID NO 66
<211> LENGTH: 16
<212> TYPE: DNA
<213> ORGANISM: Artificial Sequence
<220> FEATURE:
<223> OTHER INFORMATION: C1orf43 linear detection probe
<220> FEATURE:
<221> NAME/KEY: misc_feature
<222> LOCATION: (1)..(16)
<223> OTHER INFORMATION: N = U

<400> SEQUENCE: 66
gaagnnggng aangng                                                     16

<210> SEQ ID NO 67
<211> LENGTH: 19
```

```
<212> TYPE: DNA
<213> ORGANISM: Artificial Sequence
<220> FEATURE:
<223> OTHER INFORMATION: C1orf43 linear detection probe
<220> FEATURE:
<221> NAME/KEY: misc_feature
<222> LOCATION: (1)..(19)
<223> OTHER INFORMATION: N = U

<400> SEQUENCE: 67
gnggaanaac nnaccnnng                                              19

<210> SEQ ID NO 68
<211> LENGTH: 19
<212> TYPE: DNA
<213> ORGANISM: Artificial Sequence
<220> FEATURE:
<223> OTHER INFORMATION: C1orf43 linear detection probe
<220> FEATURE:
<221> NAME/KEY: misc_feature
<222> LOCATION: (1)..(19)
<223> OTHER INFORMATION: N = U

<400> SEQUENCE: 68
gnggggaagn nggngaang                                              19

<210> SEQ ID NO 69
<211> LENGTH: 14
<212> TYPE: DNA
<213> ORGANISM: Artificial Sequence
<220> FEATURE:
<223> OTHER INFORMATION: C1orf43 linear detection probe
<220> FEATURE:
<221> NAME/KEY: misc_feature
<222> LOCATION: (1)..(14)
<223> OTHER INFORMATION: N = U

<400> SEQUENCE: 69
gaangnggaa naac                                                   14

<210> SEQ ID NO 70
<211> LENGTH: 18
<212> TYPE: DNA
<213> ORGANISM: Artificial Sequence
<220> FEATURE:
<223> OTHER INFORMATION: C1orf43 linear detection probe
<220> FEATURE:
<221> NAME/KEY: misc_feature
<222> LOCATION: (1)..(18)
<223> OTHER INFORMATION: N = U

<400> SEQUENCE: 70
cnnaccnnng ngcnccac                                               18

<210> SEQ ID NO 71
<211> LENGTH: 21
<212> TYPE: DNA
<213> ORGANISM: Artificial Sequence
<220> FEATURE:
<223> OTHER INFORMATION: C1orf43 linear detection probe
<220> FEATURE:
<221> NAME/KEY: misc_feature
<222> LOCATION: (1)..(21)
<223> OTHER INFORMATION: N = U

<400> SEQUENCE: 71
gaanaacnna ccnnngngcn c                                           21

<210> SEQ ID NO 72
```

```
<211> LENGTH: 17
<212> TYPE: DNA
<213> ORGANISM: Artificial Sequence
<220> FEATURE:
<223> OTHER INFORMATION: C1orf43 linear detection probe
<220> FEATURE:
<221> NAME/KEY: misc_feature
<222> LOCATION: (1)..(17)
<223> OTHER INFORMATION: N = U

<400> SEQUENCE: 72
gncaagnggg gaagnng                                                   17
```

COMPOSITIONS AND METHODS FOR DETECTING C1ORF43 NUCLEIC ACID

This application is a national phase entry pursuant to 35 U.S.C. § 371 of International Application No. PCT/US2018/061225, filed Nov. 15, 2018, which claims the benefit of U.S. Provisional Application No. 62/588,130, filed Nov. 17, 2017. This disclosure relates to oligomers, compositions, kits, and methods useful for the detection of C1orf43 nucleic acid.

SEQUENCE LISTING

The present application is filed with an electronically-formatted Sequence Listing. The Sequence Listing is provided as a file entitled "2020-04-29 01159-0030-00US Seq List ST25.txt" created on Apr. 29, 2020, which is 24,780 bytes in size. The information in the electronically-formatted sequence listing is incorporated herein by reference in its entirety.

INTRODUCTION AND SUMMARY

Nucleic acid-based testing is an increasingly important approach for detecting pathological or pre-pathological states such as infections, genetic abnormalities, and aberrant expression. Many tests use amplification of one or more target nucleic acids as a primary mechanism, where the presence or absence of the product(s) of the amplification ("amplicon(s)") indicates the presence or absence of a given state. The accuracy of such tests can depend on reliable controls, particularly in the case where no target product is observed. A reliable control can establish that steps up to and including the amplification and detection steps were performed without error, reducing the likelihood of false negative results.

Ideally, a control would validate as many steps of a given process as possible. For example, the detection of a control amplicon generally indicates that at least the amplification and detection steps were performed without error and that the reagents used for amplification and detection were not compromised. Where the template nucleic acid for the control amplicon is obtained from the sample itself, the presence of the control amplicon further indicates that sample collection and isolation were performed without error.

It is also desirable for a control to be widely applicable, to reduce the need to identify and validate a different control for individual tests. For example, a widely applicable control may use a template nucleic acid that is present in sufficient quantity in many cell types with little variation in genotype or expression level.

It is furthermore desirable for the reagents used to amplify the control to perform robustly with good sensitivity and specificity, so that the presence or absence of the control amplicon can be interpreted with confidence.

As described herein, oligomers, compositions, kits, and methods useful for the detection of endogenous C1orf43 nucleic acid have been developed that can meet one or more of these needs, e.g., that can be used in assays performed on a wide variety of samples, that can validate assay steps from sample isolation through detection, that can perform robustly with good sensitivity and specificity, or that at least provide the public with a useful choice.

Accordingly, the following embodiments are provided. Embodiment 1 is a combination of oligomers comprising at least first and second amplification oligomers, wherein the first and second amplification oligomers are reverse and forward amplification oligomers, respectively; each comprise at least 10 nucleotides; and are configured to specifically hybridize to first and second sites in the sequence of SEQ ID NO: 39 and generate an amplicon therefrom, respectively.

Embodiment 2 is a method of detecting the presence or absence of a C1orf43 nucleic acid in a sample, comprising:
contacting the sample with a combination of oligomers comprising at least first and second amplification oligomers,
performing a nucleic acid amplification reaction which produces at least a first amplicon in the presence of the C1orf43 nucleic acid,
and detecting the presence or absence of the first amplicon,
wherein: the first amplicon is produced through extension of the first and second amplification oligomers in the presence of the C1orf43 nucleic acid; and
wherein the first and second amplification oligomers are reverse and forward amplification oligomers, respectively; each comprise at least 10 nucleotides; and are configured to specifically hybridize to first and second sites in the sequence of SEQ ID NO: 39, respectively.

Embodiment 3 is the combination of embodiment 1 or method of embodiment 2, wherein at least one of the amplification oligomers is a promoter-primer.

Embodiment 4 is the combination or method of any one of the preceding embodiments, wherein the first amplification oligomer is a promoter-primer.

Embodiment 5 is the combination or method of any one of embodiments 3-4, wherein the promoter-primer comprises a T7 promoter which is located 5' of a target-hybridizing sequence.

Embodiment 6 is the combination or method of embodiment 5, wherein the T7 promoter comprises the sequence of SEQ ID NO: 58.

Embodiment 7 is the combination or method of any one of the preceding embodiments, wherein the first and second amplification oligomer are configured to generate an amplicon comprising at least 30, 40, 50, 60, 70, 80, 90, 100, 110, 120, 130, 140, or 144 nucleotides of the sequence of SEQ ID NO: 40.

Embodiment 8 is the combination or method of embodiment 7, wherein the first and second amplification oligomer are configured to generate an amplicon comprising the sequence of SEQ ID NO: 41.

Embodiment 9 is the combination or method of embodiment 7, wherein the first and second amplification oligomer are configured to generate an amplicon comprising the sequence of SEQ ID NO: 42.

Embodiment 10 is the combination or method of any one of the preceding embodiments, wherein the first amplification oligomer is configured to specifically hybridize to a first site in the complement of SEQ ID NO: 52.

Embodiment 11 is the combination or method of embodiment 10, wherein the first site comprises the sequence of SEQ ID NO: 53.

Embodiment 12 is the combination or method of embodiment 10, wherein the first site comprises the sequence of SEQ ID NO: 54.

Embodiment 13 is the combination or method of any one of the preceding embodiments, wherein the first amplification oligomer comprises a target-hybridizing sequence comprising the sequence of SEQ ID NO: 27, optionally with up to two mismatches.

Embodiment 14 is the combination or method of any one of embodiments 1-12, wherein the first amplification oligomer comprises a target-hybridizing sequence comprising the sequence of SEQ ID NO: 29, optionally with up to two mismatches.

Embodiment 15 is the combination or method of any one of embodiments 1-12, wherein the first amplification oligomer comprises a target-hybridizing sequence comprising the sequence of SEQ ID NO: 31, optionally with up to two mismatches.

Embodiment 16 is the combination or method of any one of embodiments 1-12, wherein the first amplification oligomer comprises a target-hybridizing sequence comprising the sequence of SEQ ID NO: 33, optionally with up to two mismatches.

Embodiment 17 is the combination or method of any one of the preceding embodiments, wherein the first amplification oligomer comprises a target-hybridizing sequence comprising the sequence of SEQ ID NO: 27, 29, 31, or 33.

Embodiment 18 is the combination or method of any one of the preceding embodiments, wherein the first amplification oligomer comprises the sequence of SEQ ID NO: 26, 28, 30, or 32.

Embodiment 19 is the combination or method of any one of the preceding embodiments, wherein the second amplification oligomer is configured to specifically hybridize to a second site in the complement of SEQ ID NO: 46.

Embodiment 20 is the combination or method of embodiment 19, wherein the second site comprises the sequence of SEQ ID NO: 47.

Embodiment 21 is the combination or method of embodiment 19, wherein the second site comprises the sequence of SEQ ID NO: 48.

Embodiment 22 is the combination or method of any one of the preceding embodiments, wherein the second amplification oligomer comprises a target-hybridizing sequence comprising the sequence of SEQ ID NO: 34, optionally with up to two mismatches.

Embodiment 23 is the combination or method of any one of embodiments 1-21, wherein the second amplification oligomer comprises a target-hybridizing sequence comprising the sequence of SEQ ID NO: 35, optionally with up to two mismatches.

Embodiment 24 is the combination or method of any one of embodiments 1-21, wherein the second amplification oligomer comprises a target-hybridizing sequence comprising the sequence of SEQ ID NO: 36, optionally with up to two mismatches.

Embodiment 25 is the combination or method of any one of embodiments 1-21, wherein the second amplification oligomer comprises a target-hybridizing sequence comprising the sequence of SEQ ID NO: 37, optionally with up to two mismatches.

Embodiment 26 is the combination or method of any one of embodiments 1-21, wherein the second amplification oligomer comprises a target-hybridizing sequence comprising the sequence of SEQ ID NO: 38, optionally with up to two mismatches.

Embodiment 27 is the combination or method of any one of the preceding embodiments, wherein the second amplification oligomer comprises a target-hybridizing sequence comprising the sequence of SEQ ID NO: 34, 35, 36, 37, or 38.

Embodiment 28 is the combination or method of any one of the preceding embodiments, wherein the combination further comprises at least one probe oligomer that comprises at least 10 nucleotides and is configured to specifically hybridize to an amplicon produced from the first and second amplification oligomers.

Embodiment 29 is the combination or method of embodiment 28, wherein the probe oligomer is configured to specifically hybridize to a detection site in a nucleic acid having the sequence of SEQ ID NO: 43.

Embodiment 30 is a probe oligomer that comprises at least 10 nucleotides and is configured to specifically hybridize to a detection site in a nucleic acid having the sequence of SEQ ID NO: 43.

Embodiment 31 is the combination, method, or probe oligomer of any one of embodiments 28-30, wherein the probe oligomer is configured to specifically hybridize to a detection site in the sequence of SEQ ID NO: 44.

Embodiment 32 is the combination, method, or probe oligomer of any one of embodiments 28-30, wherein the probe oligomer is configured to specifically hybridize to a detection site in a nucleic acid having the sequence of SEQ ID NO: 45.

Embodiment 33 is the combination, method, or probe oligomer of any one of embodiments 28-30, wherein the probe oligomer is configured to specifically hybridize to a detection site in a nucleic acid having the sequence of SEQ ID NO: 49.

Embodiment 34 is the combination, method, or probe oligomer of embodiment 33, wherein the probe oligomer comprises a target hybridizing sequence comprising the sequence of SEQ ID NO: 50.

Embodiment 35 is the combination, method, or probe oligomer of embodiment 33, wherein the probe oligomer comprises a target hybridizing sequence comprising the sequence of SEQ ID NO: 51.

Embodiment 36 is the combination, method, or probe oligomer of any one of embodiments 28-35, wherein the probe oligomer comprises a target hybridizing sequence comprising the sequence of SEQ ID NO: 15 with up to two mismatches.

Embodiment 37 is the combination, method, or probe oligomer of any one of embodiments 28-35, wherein the probe oligomer comprises a target hybridizing sequence comprising the sequence of SEQ ID NO: 17 with up to two mismatches.

Embodiment 38 is the combination, method, or probe oligomer of any one of embodiments 28-35, wherein the probe oligomer comprises a target hybridizing sequence comprising the sequence of SEQ ID NO: 19 with up to two mismatches.

Embodiment 39 is the combination, method, or probe oligomer of any one of embodiments 28-35, wherein the probe oligomer comprises a target hybridizing sequence comprising the sequence of SEQ ID NO: 21 with up to two mismatches.

Embodiment 40 is the combination, method, or probe oligomer of any one of embodiments 28-35, wherein the probe oligomer comprises a target hybridizing sequence comprising the sequence of SEQ ID NO: 23 with up to two mismatches.

Embodiment 41 is the combination, method, or probe oligomer of any one of embodiments 28-35, wherein the probe oligomer comprises a target hybridizing sequence comprising the sequence of SEQ ID NO: 25 with up to two mismatches.

Embodiment 42 is the combination, method, or probe oligomer of any one of embodiments 28-41, wherein the probe oligomer comprises a target hybridizing sequence comprising the sequence of SEQ ID NO: 15, 17, 19, 21, 23, or 25.

Embodiment 43 is the combination, method, or probe oligomer of any one of embodiments 28-41, wherein the probe oligomer comprises the sequence of SEQ ID NO: 14, 16, 18, 20, 22, or 24.

Embodiment 44 is the combination, method, or probe oligomer of any one of embodiments 28-35, wherein the probe oligomer comprises a target hybridizing sequence comprising the sequence of SEQ ID NO: 59 with up to two mismatches.

Embodiment 45 is the combination, method, or probe oligomer of any one of embodiments 28-35, wherein the probe oligomer comprises a target hybridizing sequence comprising the sequence of SEQ ID NO: 60 with up to two mismatches.

Embodiment 46 is the combination, method, or probe oligomer of any one of embodiments 28-35, wherein the probe oligomer comprises a target hybridizing sequence comprising the sequence of SEQ ID NO: 64 with up to two mismatches.

Embodiment 47 is the combination, method, or probe oligomer of any one of embodiments 28-35, wherein the probe oligomer comprises a target hybridizing sequence comprising the sequence of SEQ ID NO: 66 with up to two mismatches.

Embodiment 48 is the combination, method, or probe oligomer of any one of embodiments 28-35, wherein the probe oligomer comprises a target hybridizing sequence comprising the sequence of SEQ ID NO: 67 with up to two mismatches.

Embodiment 49 is the combination, method, or probe oligomer of any one of embodiments 28-35, wherein the probe oligomer comprises a target hybridizing sequence comprising the sequence of SEQ ID NO: 68 with up to two mismatches.

Embodiment 50 is the combination, method, or probe oligomer of any one of embodiments 28-35, wherein the probe oligomer comprises a target hybridizing sequence comprising the sequence of SEQ ID NO: 69 with up to two mismatches.

Embodiment 51 is the combination, method, or probe oligomer of any one of embodiments 28-35, wherein the probe oligomer comprises a target hybridizing sequence comprising the sequence of SEQ ID NO: 70 with up to two mismatches.

Embodiment 52 is the combination, method, or probe oligomer of any one of embodiments 28-35, wherein the probe oligomer comprises a target hybridizing sequence comprising the sequence of SEQ ID NO: 71 with up to two mismatches.

Embodiment 53 is the combination, method, or probe oligomer of any one of embodiments 28-35, wherein the probe oligomer comprises a target hybridizing sequence comprising the sequence of SEQ ID NO: 72 with up to two mismatches.

Embodiment 54 is a probe oligomer that comprises a target hybridizing sequence comprising the sequence of any one of SEQ ID NO: 61, 62, 63, or 65 with up to two mismatches.

Embodiment 55 is the combination, method, or probe oligomer of any one of embodiments 28 or 54, wherein the probe oligomer comprises a target hybridizing sequence comprising the sequence of SEQ ID NO: 61 with up to two mismatches.

Embodiment 56 is the combination, method, or probe oligomer of any one of embodiments 28 or 54, wherein the probe oligomer comprises a target hybridizing sequence comprising the sequence of SEQ ID NO: 62 with up to two mismatches.

Embodiment 57 is the combination, method, or probe oligomer of any one of embodiments 28 or 54, wherein the probe oligomer comprises a target hybridizing sequence comprising the sequence of SEQ ID NO: 63 with up to two mismatches.

Embodiment 58 is the combination, method, or probe oligomer of any one of embodiments 28 or 54, wherein the probe oligomer comprises a target hybridizing sequence comprising the sequence of SEQ ID NO: 65 with up to two mismatches.

Embodiment 59 is the combination, method, or probe oligomer of any one of embodiments 28-35 or 44-58, wherein the probe oligomer comprises a target hybridizing sequence comprising the sequence of any one of SEQ ID NOs: 59-72.

Embodiment 60 is the combination, method, or probe oligomer of any one of embodiments 28-59, wherein the probe oligomer comprises 2'-O-methyl-ribose in its backbone.

Embodiment 61 is the combination, method, or probe oligomer of embodiment 60, wherein at least half, at least 90%, or all of the sugars in the probe oligomer are 2'-O-methyl-ribose.

Embodiment 62 is the combination or method of any one of embodiments 1-27, wherein one or more of the first and second amplification oligomers comprises a non-nucleotide detectable label.

Embodiment 63 is the combination, method, or probe oligomer of any one of embodiments 28-61, wherein at least one probe oligomer comprises a non-nucleotide detectable label.

Embodiment 64 is the combination, method, or probe oligomer of any one of embodiments 62-63, wherein the non-nucleotide detectable label is a fluorescent label.

Embodiment 65 is the combination, method, or probe oligomer of embodiment 63 or 64, wherein the probe oligomer comprises a quencher.

Embodiment 66 is the combination, method, or probe oligomer of embodiment 65, wherein the non-nucleotide detectable label is a fluorescent label and the quencher absorbs fluorescence to a greater extent when the probe is free than when the probe is annealed to a target nucleic acid.

Embodiment 67 is the combination, method, or probe oligomer of any one of embodiments 64-66, wherein the fluorescent label is FAM, HEX, or acridine.

Embodiment 68 is the combination, method, or probe oligomer of any one of embodiments 65-67, wherein the quencher is DABCYL or ROX.

Embodiment 69 is the combination, method, or probe oligomer of any one of embodiments 65-68, wherein the fluorescent label is attached to the 5'-terminus of the probe oligomer and the quencher is attached to the 3'-terminus of the probe oligomer, or the fluorescent label is attached to the 3'-terminus of the probe oligomer and the quencher is attached to the 5'-terminus of the probe oligomer.

Embodiment 70 is the combination, method, or probe oligomer of any one of embodiments 62-63, wherein the non-nucleotide detectable label is a chemiluminescent label.

Embodiment 71 is the combination, method, or probe oligomer of any one of embodiments 28-61 or 63-70, wherein the probe oligomer comprises a first self-complementary region at its 5' end and a second self-complementary region at its 3' end.

Embodiment 72 is the combination, method, or probe oligomer of embodiment 71, wherein the self-complementary regions can hybridize to form 3 to 7 Watson-Crick or wobble base pairs.

Embodiment 73 is the combination, method, or probe oligomer of embodiment 71, wherein the self-complementary regions can hybridize to form 4 Watson-Crick or wobble base pairs.

Embodiment 74 is the combination, method, or probe oligomer of any one of embodiments 63-71, wherein the probe oligomer is a linear probe oligomer.

Embodiment 75 is a method of detecting the presence or absence of a C1orf43 nucleic acid in a sample, comprising:
contacting the sample with the probe oligomer of any one of embodiments 30-61 or 63-74; performing a hybridization reaction which produces a complex of the probe oligomer and the C1orf43 nucleic acid in the presence of the C1orf43 nucleic acid;
and detecting the presence or absence of the complex of the probe oligomer and the C1orf43 nucleic acid.

Embodiment 76 is the method of embodiment 75, wherein the hybridization reaction is a hybridization protection assay.

Embodiment 77 is the method of embodiment 75 or 76, wherein the hybridization reaction is a dual kinetic assay.

Embodiment 78 is the method of any one of embodiments 75-77, wherein the probe oligomer functions as a flasher probe in the dual kinetic assay.

Embodiment 79 is the method of any one of embodiments 75-77, wherein the probe oligomer functions as a glower probe in the dual kinetic assay.

Embodiment 80 is the method of any one of embodiments 75-79, wherein the C1orf43 nucleic acid comprises a C1orf43 amplicon.

Embodiment 81 is the method of any one of embodiments 75-79, wherein the C1orf43 nucleic acid comprises C1orf43 RNA from cells in the sample.

Embodiment 82 is the method of any one of embodiments 75-81, wherein the sample is contacted with a combination of oligomers comprising the probe oligomer.

Embodiment 83 is the combination or method of any one of embodiments 1-29, 31-56, or 82, wherein the combination further comprises at least one capture oligomer that comprises at least 10 nucleotides and is configured to specifically hybridize to a capture site in a C1orf43 nucleic acid.

Embodiment 84 is the combination or method of embodiment 83, wherein the capture site is in the sequence of SEQ ID NO: 1, 2, or 3.

Embodiment 85 is the combination or method of embodiment 83, wherein the capture site is in the sequence of SEQ ID NO: 39.

Embodiment 86 is a method of isolating C1orf43 nucleic acid from a sample, comprising:
contacting the sample with at least one capture oligomer under conditions permissive for forming one or more complexes of a capture oligomer and the C1orf43 nucleic acid, thereby forming a composition, wherein the capture oligomer comprises at least 10 nucleotides and is configured to specifically hybridize to a capture site in the sequence of SEQ ID NO: 39; and isolating the capture oligomer from the composition.

Embodiment 87 is the method of embodiment 86, wherein isolating the capture oligomers comprises associating the capture oligomers with a solid support, and washing the solid support.

Embodiment 88 is the method of embodiment 87, wherein the solid support comprises a poly-N sequence that is complementary to a portion of the capture oligomer.

Embodiment 89 is the method of embodiment 87, wherein the solid support comprises a binding agent that recognizes an affinity tag present in the capture oligomer.

Embodiment 90 is a capture oligomer that comprises at least 10 nucleotides and is configured to specifically hybridize to a capture site in the sequence of SEQ ID NO: 39.

Embodiment 91 is the combination, method, or capture oligomer of any one of embodiments 83-90, wherein the capture site is in the sequence of SEQ ID NO: 55.

Embodiment 92 is the combination, method, or capture oligomer of any one of embodiments 83-90, wherein the capture oligomer comprises a target hybridizing sequence comprising the sequence of SEQ ID NO: 56.

Embodiment 93 is the combination, method, or capture oligomer of any one of embodiments 83-90, wherein the capture oligomer comprises a target hybridizing sequence comprising the sequence of SEQ ID NO: 57.

Embodiment 94 is the combination, method, or capture oligomer of any one of embodiments 83-93, wherein the capture oligomer comprises a target hybridizing sequence comprising the sequence of SEQ ID NO: 5 with up to two mismatches.

Embodiment 95 is the combination, method, or capture oligomer of any one of embodiments 83-93, wherein the capture oligomer comprises a target hybridizing sequence comprising the sequence of SEQ ID NO: 7 with up to two mismatches.

Embodiment 96 is the combination, method, or capture oligomer of any one of embodiments 83-93, wherein the capture oligomer comprises a target hybridizing sequence comprising the sequence of SEQ ID NO: 9 with up to two mismatches.

Embodiment 97 is the combination, method, or capture oligomer of any one of embodiments 83-93, wherein the capture oligomer comprises a target hybridizing sequence comprising the sequence of SEQ ID NO: 11 with up to two mismatches.

Embodiment 98 is the combination, method, or capture oligomer of any one of embodiments 83-93, wherein the capture oligomer comprises a target hybridizing sequence comprising the sequence of SEQ ID NO: 13 with up to two mismatches.

Embodiment 99 is the combination, method, or capture oligomer of any one of embodiments 83-93, wherein the capture oligomer comprises a target hybridizing sequence comprising the sequence of SEQ ID NO: 5, 7, 9, 11, or 13.

Embodiment 100 is the combination, method, or capture oligomer of any one of embodiments 83-99, wherein the capture oligomer comprises the sequence of SEQ ID NO: 4, 6, 8, 10, or 12.

Embodiment 101 is the combination, method, or capture oligomer of any one of embodiments 83-100, wherein the capture oligomer comprises 2'-O-methyl-ribose in its backbone.

Embodiment 102 is the combination, method, or capture oligomer of embodiment 101, wherein at least half, at least 90%, or all of the sugars in the target hybridizing sequence of the capture oligomer are 2'-O-methyl-ribose.

Embodiment 103 is the combination, method, or capture oligomer of any one of embodiments 83-102, wherein the capture oligomer further comprises a non-nucleotide affinity label.

Embodiment 104 is the combination, method, or capture oligomer of any one of embodiments 83-102, wherein the capture oligomer further comprises a non-C1orf43 sequence.

Embodiment 105 is the combination, method, or capture oligomer of embodiment 104, wherein the non-C1orf43 sequence is a poly-N sequence.

Embodiment 106 is the combination, method, or capture oligomer of embodiment 105, wherein the poly-N sequence is a poly-A or poly-T sequence.

Embodiment 107 is a combination comprising the capture oligomer according to any one of embodiments 90-106 and one or more amplification oligomers, wherein the amplification oligomer is configured to specifically hybridize to a site in the sequence of SEQ ID NO: 39.

Embodiment 108 is the combination of embodiment 107, wherein the one or more amplification oligomers includes the first amplification oligomer as recited in any one of embodiments 4-18.

Embodiment 109 is the combination of embodiment 107 or 108, wherein the one or more amplification oligomers includes the second amplification oligomer as recited in any one of embodiments 19-27.

Embodiment 110 is the combination of any one of embodiments 107-109, further comprising the probe oligomer as recited in any one of embodiments 28-61 or 63-74.

Embodiment 111 is the method of any one of embodiments 86-89 or 91-106, further comprising performing a linear amplification wherein at least one amplification oligomer is extended.

Embodiment 112 is the method of embodiment 111, wherein prior to the linear amplification, the amplification oligomer is associated with a complex of C1orf43 nucleic acid and a capture oligomer and the complex is associated with a solid support, and the method comprises washing the solid support.

Embodiment 113 is the method of embodiment 112, wherein the solid support is a population of microbeads.

Embodiment 114 is the method of embodiment 113, wherein the microbeads of the population are magnetic.

Embodiment 115 is the method of any one of embodiments 112-114, wherein following the washing step, the method comprises adding one or more additional amplification oligomers oppositely oriented to an amplification oligomer associated with the complex of C1orf43 nucleic acid and the capture oligomer.

Embodiment 116 is the method of embodiment 115, wherein the one or more oppositely oriented additional amplification oligomers includes a promoter-primer.

Embodiment 117 is the method of embodiment 116, wherein the one or more oppositely oriented additional amplification oligomers includes an oligomer that is not a promoter-primer.

Embodiment 118 is the method of any one of embodiments 115-117, wherein the one or more oppositely oriented additional amplification oligomers includes the second amplification oligomer as recited in any one of embodiments 19-27.

Embodiment 119 is the method of any one of embodiments 115-118, further comprising performing an exponential amplification following the linear amplification.

Embodiment 120 is the method of embodiment 119, wherein the exponential amplification is transcription-mediated amplification.

Embodiment 121 is the method of any one of embodiments 2-29, 31-89, 91-105, or 111-120, further comprising quantifying C1orf43 nucleic acid in the sample.

Embodiment 122 is a kit or composition comprising at least one, two, three, or four of a first amplification oligomer, a second amplification oligomer, a probe oligomer, or a capture oligomer recited in any one of the preceding embodiments.

Embodiment 123 is the kit or composition of embodiment 122, comprising at least one probe oligomer as recited in any one of embodiments 28-61 or 63-74.

Embodiment 124 is the kit or composition of any one of embodiments 122-123, comprising at least one capture oligomer as recited in any one of embodiments 83-85 or 90-106.

Embodiment 125 is the kit or composition of any one of embodiments 122-124, comprising the first amplification oligomer as recited in any one of embodiments 4-18 and the second amplification oligomer as recited in any one of embodiments 19-27.

Embodiment 126 is a kit according to any one of embodiments 122-125 or comprising the combination of any one of embodiments 1, 3-62, 63-85, or 91-110.

Embodiment 127 is a composition according to any one of embodiments 122-125 or comprising the combination of any one of embodiments 1, 3-62, 63-85, or 91-110.

Embodiment 128 is the composition of embodiment 127, which is aqueous, frozen, or lyophilized.

Embodiment 129 is the use of the combination, method, composition, capture oligomer, probe oligomer, or kit of any one of the preceding embodiments for detecting the presence or absence of a C1orf43 nucleic acid in a sample.

Embodiment 130 is the combination, method, composition, capture oligomer, probe oligomer, or kit of any one of embodiments 1-128, for use in detecting the presence or absence of a C1orf43 nucleic acid in a sample.

Embodiment 131 is the use of the combination, method, composition, capture oligomer, probe oligomer, or kit of any one of embodiments 1-128 for quantifying a C1orf43 nucleic acid in a sample.

Embodiment 132 is the combination, method, composition, capture oligomer, probe oligomer, or kit of any one of embodiments 1-128, for use in quantifying a C1orf43 nucleic acid in a sample.

Embodiment 133 is the use, combination, method, composition, capture oligomer, probe oligomer, or kit of any one of embodiments 2-29, 31-53, 55-89, 91-106, 111-121, or 126-132, wherein the sample comprises human mRNA.

Embodiment 134 is the use, combination, method, composition, or kit of embodiment 133, wherein the human mRNA comprises mRNA from bladder, ductus deferens, epididymis, kidney, lymph node, pancreas, peripheral blood lymphocytes, penis, prostate, seminal vesicle, or spleen.

Embodiment 135 is the use, combination, method, composition, or kit of embodiment 133, wherein the human mRNA comprises mRNA from a vaginal or cervical sample.

Embodiment 136 is the use, combination, method, composition, or kit of embodiment 135, wherein the vaginal or cervical sample is a vaginal or cervical swab.

Embodiment 137 is the use, combination, method, composition, or kit of any one of embodiments 2-29, 31-53, 55-89, 91-106, 111-121, or 126-136, wherein the method or use further comprises detecting the presence or absence of at least one nucleic acid of a microbe or pathogen.

Embodiment 138 is the use, combination, method, composition, or kit of embodiment 137, wherein the at least one nucleic acid of a microbe or pathogen comprises human papillomavirus nucleic acid, *Chlamydia trachomatis* nucleic acid, *Neisseria gonorrheae* nucleic acid, *Trichomonas vaginalis* nucleic acid, or *Mycoplasma genitalium* nucleic acid.

Embodiment 139 is the use, combination, method, composition, or kit of any one of embodiments 2-29, 31-53, 55-89, 91-106, 111-121, or 126-138, wherein the method or use further comprises detecting the presence or absence of at least one mRNA other than C1orf43.

Embodiment 140 is the use, combination, method, composition, or kit of embodiment 139, wherein the mRNA other than C1orf43 is a human mRNA other than C1orf43.

DETAILED DESCRIPTION OF CERTAIN EMBODIMENTS

A. Overview

As demonstrated below in the examples, it has been found that C1orf43 is expressed in a wide variety of tissues, and oligomers have been developed that can detect and quantify C1orf43 in a sensitive and specific manner. Accordingly, this disclosure provides oligomers, compositions, kits, and methods useful for the detection of C1orf43 nucleic acid. Detection of C1orf43 can be used as a positive control in combination with nucleic acid assays on samples that should contain C1orf43 nucleic acid (e.g., C1orf43 mRNA), such as samples that should contain mammalian, primate, or human tissue or cells. Detection of C1orf43 can validate such assays by allowing a negative result for an analyte of interest to be interpreted with confidence as a true negative result and not a false negative resulting from a failure in one or more of sample acquisition, nucleic acid isolation, amplification, and/or probe detection.

Thus, for example, embodiments provided herein include a combination of at least two amplification oligomers for amplifying a C1orf43 amplicon within or comprising the region of C1orf43 shown as SEQ ID NO: 39 and a detection oligomer for detecting the C1orf43 amplicon is provided, which optionally further comprises at least one capture oligomer for isolating C1orf43 nucleic acid from a sample. In a further embodiment, the amplification oligomers are for an amplification reaction that begins with C1orf43 mRNA, for example, transcription-mediated amplification.

B. Definitions

Before describing the present teachings in detail, it is to be understood that the disclosure is not limited to specific compositions or process steps, as such may vary. Measured and measureable values are understood to be approximate, taking into account significant digits and the error associated with the measurement. It should be noted that, as used in this specification and the appended claims, the singular form "a", "an" and "the" include plural references unless the context clearly dictates otherwise. Thus, for example, reference to "an oligomer" includes a plurality of oligomers and the like.

The terms "comprise", "comprises", "comprising", "contain", "contains", "containing", "include", "includes", and "including" are open-ended and not intended to be limiting. Unless specifically noted, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

It is to be understood that both the foregoing general description and detailed description are exemplary and explanatory only and are not restrictive of the teachings. To the extent that any material incorporated by reference is inconsistent with the express content of this disclosure, the express content controls. Section headings are provided for the convenience of the reader and do not limit the scope of the disclosure.

"Sample" includes any specimen (e.g., biological, environmental, synthetic, or forensic) that may contain C1orf43 nucleic acid. "Biological samples" include any tissue or material derived from a living or dead subject (e.g., mammal, primate, or human; also contemplated are transgenic cells or organisms comprising C1orf43 nucleic acid) that may contain C1orf43 nucleic acid, including, e.g., peripheral blood, plasma, serum, bladder, ductus deferens, epididymis, kidney, lymph node, pancreas, peripheral blood lymphocytes, penis, prostate, seminal vesicle, spleen, vaginal or cervical samples (e.g., swabs), or other body fluids or materials. The biological sample may be treated to physically or mechanically disrupt tissue or cell structure, thus releasing intracellular components into a solution which may further contain enzymes, buffers, salts, detergents and the like, which are used to prepare a biological sample for analysis. Also, samples may include processed samples, such as those obtained from passing samples over or through a filtering device, or following centrifugation, or by adherence to a medium, matrix, or support.

"Nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid "backbone" may be made up of a variety of linkages, including one or more of sugar-phosphodiester linkages, peptide-nucleic acid bonds (in "peptide nucleic acids" or PNAs, see, e.g., International Patent Application Pub. No. WO 95/32305), phosphorothioate linkages, methylphosphonate linkages, or combinations thereof. Sugar moieties of the nucleic acid may be either ribose or deoxyribose, or similar compounds having known substitutions such as, for example, 2'-methoxy substitutions and 2'-halide substitutions (e.g., 2'-F). Nitrogenous bases may be conventional bases (A, G, C, T, U), analogs thereof (e.g., inosine, 5-methylisocytosine, isoguanine; see, e.g., The Biochemistry of the Nucleic Acids 5-36, Adams et al., ed., 11th ed., 1992; Abraham et al., 2007, BioTechniques 43: 617-24), which include derivatives of purine or pyrimidine bases (e.g., $N^4$-methyl deoxygaunosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, and pyrazolo-compounds, such as unsubstituted or 3-substituted pyrazolo [3,4-d]pyrimidine; U.S. Pat. Nos. 5,378,825, 6,949,367 and International Patent Application Pub. No. WO 93/13121, each incorporated by reference herein). Nucleic acids may include "abasic" residues in which the backbone does not include a nitrogenous base for one or more residues (see. e.g., U.S. Pat. No. 5,585,481, incorporated by reference herein). A nucleic acid may comprise only conventional sugars, bases, and linkages as found in RNA and DNA, or may include conventional components and substitutions (e.g., conventional bases linked by a 2'-methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et al., Biochemistry 43:13233-41, 2004, incorporated by reference herein). Nucleic acids may include modified bases to alter the function or behavior of the nucleic acid, e.g., addition of a 3'-terminal dideoxynucleotide to block additional nucleotides from being added to the nucleic acid. Synthetic methods for making nucleic acids in vitro are well-known in the art although nucleic acids may be purified from natural sources using routine techniques.

A "C1orf43 nucleic acid" is a nucleic acid that occurs in, is at least 90% or at least 95% identical to, or contains no more than one mismatch relative to any allele of C1orf43, such that, for example, "14 contiguous nucleotides of C1orf43 nucleic acid sequence" refers to a 14-mer that matches at least 13 out of 14 positions of an allele of C1orf43 (including the coding strand or the complement thereof). The presence of a U is considered equivalent to a T and vice versa for purposes of determining whether a sequence qualifies as a C1orf43 nucleic acid sequence. The target-hybridizing regions of exemplary oligomers disclosed herein, the C1orf43-derived sequence of in vitro transcripts disclosed herein, and subsequences thereof are also considered C1orf43 nucleic sequence. Thus, examples of C1orf43 sequence include SEQ ID NOs: 1-3, 39-57, and any sequences identified herein as target-hybridizing sequences, and complements thereof. Percent identity can be determined using an appropriate alignment algorithm such as the Needleman-Wunsch algorithm with standard parameters.

The term "polynucleotide" as used herein denotes a nucleic acid chain. Throughout this application, nucleic acids are designated by the 5'-terminus to the 3'-terminus. Synthetic nucleic acids, e.g., DNA, RNA, DNA/RNA chimerics, (including when non-natural nucleotides or analogues are included therein), are typically synthesized "3'-to-5'," i.e., by the addition of nucleotides to the 5'-terminus of a growing nucleic acid. A polynucleotide or oligomer is considered to comprise two (or more) specified SEQ ID NOs if each of the sequence of the SEQ ID NOs is present, regardless of whether they overlap. Thus, as a simplified example, the sequence CAT comprises both CA and AT.

A "nucleotide" as used herein is a subunit of a nucleic acid consisting of a phosphate group, a 5-carbon sugar, and a nitrogenous base (also referred to herein as "nucleobase"). The 5-carbon sugar found in RNA is ribose. In DNA, the 5-carbon sugar is 2'-deoxyribose. The term also includes analogs of such subunits, such as a methoxy group at the 2' position of the ribose (also referred to herein as "2'-O-Me" or "2'-methoxy"). As used herein, methoxy oligonucleotides containing "T" residues have a methoxy group at the 2' position of the ribose moiety, and a uracil at the base position of the nucleotide.

A "non-nucleotide unit" as used herein is a unit that does not significantly participate in hybridization of a polymer. Such units do not, for example, participate in any significant hydrogen bonding with a nucleotide, and would exclude units having as a component one of the five nucleotide bases or analogs thereof.

A "target nucleic acid" as used herein is a nucleic acid comprising a target sequence to be amplified. Target nucleic acids may be DNA or RNA as described herein, and may be either single-stranded or double-stranded. The target nucleic acid may include other sequences besides the target sequence, which may not be amplified.

The term "target sequence" as used herein refers to the particular nucleotide sequence of the target nucleic acid that is to be amplified and/or detected. The "target sequence" includes the complexing sequences to which oligonucleotides (e.g., priming oligonucleotides and/or promoter oligonucleotides) complex during an amplification processes (e.g., TMA). Where the target nucleic acid is originally single-stranded, the term "target sequence" will also refer to the sequence complementary to the "target sequence" as present in the target nucleic acid. Where the target nucleic acid is originally double-stranded, the term "target sequence" refers to both the sense or coding (+) and antisense or template (−) strands. The (+) strand corresponds to the mRNA sequence and the (−) is the complement thereof. The exemplary sequence of SEQ ID NO: 1 represents a (+) strand.

"Target-hybridizing sequence" is used herein to refer to the portion of an oligomer that is configured to hybridize with a target sequence. In some embodiments, the target-hybridizing sequences are configured to specifically hybridize with a target nucleic acid sequence. Target-hybridizing sequences may be 100% complementary to the portion of the target sequence to which they are configured to hybridize, but not necessarily. Target-hybridizing sequences may also include inserted, deleted and/or substituted nucleotide residues relative to a target sequence. Less than 100% complementarity of a target-hybridizing sequence to a target sequence may arise, for example, when the target nucleic acid comprises one or more polymorphic positions (e.g., SNPs), such as would be the case for an oligomer configured to hybridize to various alleles of C1orf43. It is understood that other reasons exist for configuring a target-hybridizing sequence to have less than 100% complementarity to a target nucleic acid.

The term "configured to" denotes an actual arrangement of the polynucleotide sequence configuration of a referenced oligonucleotide target-hybridizing sequence. For example, amplification oligomers that are "configured to generate an amplicon" have polynucleotide sequences that hybridize to the target sequence and can be used in an amplification reaction to generate the amplicon; for example, in the context of PCR or TMA reactions, the oligomers have hybridization sites bounding at least one nucleotide and their 3' ends are properly oriented for amplification when hybridized.

The term "configured to specifically hybridize to" as used herein means that the target-hybridizing region of an amplification oligonucleotide, detection probe, or other oligonucleotide has a polynucleotide sequence that could target a sequence of the referenced target region. Such an oligonucleotide is not limited to targeting that sequence only, but is rather useful as a composition, in a kit, or in a method for targeting the target nucleic acid. The oligonucleotide can function as a component of an assay for amplification and detection of C1orf43 from a sample, and therefore can target C1orf43 in the presence of other nucleic acids commonly found in testing samples. "Specifically hybridize to" does not mean exclusively hybridize to, as some small level of hybridization to non-target nucleic acids may occur, as is understood in the art. Rather, "specifically hybridize to" means that the oligonucleotide is configured to function in an assay to primarily hybridize the target so that an accurate detection of target nucleic acid in a sample can be determined. Unless the context indicates otherwise, an oligomer is considered to specifically hybridize to a given sequence if it specifically hybridizes to either strand of a double-stranded version of that sequence.

The interchangeable terms "oligomer," "oligo," and "oligonucleotide" refer to a nucleic acid having generally less than 1,000 nucleotide (nt) residues, including polymers in a range having a lower limit of 5 nt residues and an upper limit of 500 to 900 nt residues. In some embodiments, oligonucleotides are in a size range having a lower limit of 12 to 15 nt and an upper limit of 50 to 600 nt, and other embodiments are in a range having a lower limit of 15 to 20 nt and an upper limit of 22 to 100 nt. Oligonucleotides may be purified from naturally occurring sources or may be synthesized using any of a variety of well-known enzymatic or chemical methods. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase; it may function as a primer and provide a promoter if it contains a sequence recognized by an RNA polymerase and allows for transcription (e.g., a T7 Primer); and it may function to detect a target nucleic acid if it is capable of hybridizing to the target nucleic acid, or an amplicon thereof, and further provides a detectible moiety (e.g., a fluorophore).

As used herein, a "blocking moiety" is a substance used to "block" the 3'-terminus of an oligonucleotide or other nucleic acid so that it cannot be efficiently extended by a nucleic acid polymerase. Oligomers not intended for extension by a nucleic acid polymerase may include a blocker group that replaces the 3' OH to prevent enzyme-mediated extension of the oligomer in an amplification reaction. For example, blocked amplification oligomers and/or detection probes present during amplification may not have functional 3' OH and instead include one or more blocking groups located at or near the 3' end. In some embodiments, a blocking group near the 3' end and may be within five residues of the 3' end and is sufficiently large to limit binding of a polymerase to the oligomer. In other embodiments, a blocking group is covalently attached to the 3' terminus. Many different chemical groups may be used to block the 3' end, e.g., alkyl or substituted alkyl groups (e.g., hexanediol), non-nucleotide linkers, alkane-diol dideoxynucleotide residues, and cordycepin.

An "amplification oligomer" is an oligomer, at least the 3'-end of which is complementary to a target nucleic acid, and which hybridizes to a target nucleic acid, or its complement, and participates in a nucleic acid amplification reaction. An example of an amplification oligomer is a "primer" that hybridizes to a target nucleic acid and contains a 3' OH end that is extended by a polymerase in an amplification process. In some embodiments, the 5' region of an amplification oligonucleotide may include a promoter sequence that is non-complementary to the target nucleic acid (which may be referred to as a "promoter primer"). Another example of an amplification oligomer is an oligomer that is not extended by a polymerase (e.g., because it has a 3' blocked end) but participates in or facilitates amplification. For example, the 5' region of an amplification oligonucleotide may include a promoter sequence that is non-complementary to the target nucleic acid (which may be referred to as a "promoter provider"). Those skilled in the art will understand that an amplification oligomer that functions as a primer may be modified to include a 5' promoter sequence, and thus function as a promoter primer. Incorporating a 3' blocked end further modifies the promoter primer, which is now capable of hybridizing to a target nucleic acid and providing an upstream promoter sequence that serves to initiate transcription, but does not provide a primer for oligo extension. Such a modified oligo is referred to herein as a "promoter provider" oligomer. Size ranges for amplification oligonucleotides include those that are 10 to 70 nt long (not including any promoter sequence or poly-A tails) and contain at least 10 contiguous bases, or even at least 12 contiguous bases that are complementary to a region of the target nucleic acid sequence (or a complementary strand thereof). The contiguous bases are at least 80%, or at least 90%, or completely complementary to the target sequence to which the amplification oligomer binds. An amplification oligomer may optionally include modified nucleotides or analogs, or additional nucleotides that participate in an amplification reaction but are not complementary to or contained in the target nucleic acid, or template sequence. It is understood that when referring to ranges for the length of an oligonucleotide, amplicon, or other nucleic acid, that the range is inclusive of all whole numbers (e.g., 19-25 contiguous nucleotides in length includes 19, 20, 21, 22, 23, 24 & 25).

As used herein, a "promoter" is a specific nucleic acid sequence that is recognized by a DNA-dependent RNA polymerase ("transcriptase") as a signal to bind to the nucleic acid and begin the transcription of RNA at a specific site.

"Amplification" refers to any known procedure for obtaining multiple copies of a target nucleic acid sequence or its complement or fragments thereof. The multiple copies may be referred to as amplicons or amplification products. Amplification of "fragments" refers to production of an amplified nucleic acid that contains less than the complete target nucleic acid or its complement, e.g., produced by using an amplification oligonucleotide that hybridizes to, and initiates polymerization from, an internal position of the target nucleic acid. Known amplification methods include, for example, replicase-mediated amplification, polymerase chain reaction (PCR), ligase chain reaction (LCR), strand-displacement amplification (SDA), and transcription-mediated or transcription-associated amplification. Replicase-mediated amplification uses self-replicating RNA molecules, and a replicase such as QB-replicase (see. e.g., U.S. Pat. No. 4,786,600, incorporated by reference herein). PCR amplification uses a DNA polymerase, pairs of primers, and thermal cycling to synthesize multiple copies of two complementary strands of dsDNA or from a cDNA (see. e.g., U.S. Pat. Nos. 4,683,195; 4,683,202; and 4,800,159; each incorporated by reference herein). LCR amplification uses four or more different oligonucleotides to amplify a target and its complementary strand by using multiple cycles of hybridization, ligation, and denaturation (see. e.g., U.S. Pat. Nos. 5,427,930 and 5,516,663, each incorporated by reference herein). SDA uses a primer that contains a recognition site for a restriction endonuclease and an endonuclease that nicks one strand of a hemimodified DNA duplex that includes the target sequence, whereby amplification occurs in a series of primer extension and strand displacement steps (see. e.g., U.S. Pat. Nos. 5,422,252; 5,547,861; and 5,648,211; each incorporated by reference herein).

As used herein, the term "linear amplification" refers to an amplification mechanism that is designed to produce an increase in the target nucleic acid linearly proportional to the amount of target nucleic acid in the reaction. For instance, multiple RNA copies can be made from a DNA target using a transcription-associated reaction, where the increase in the number of copies can be described by a linear factor (e.g., starting copies of template×100). In some embodiments, a first phase linear amplification in a multiphase amplification procedure increases the starting number of target nucleic acid strands or the complements thereof by at least 10 fold, e.g., by at least 100 fold, or by 10 to 1,000 fold before the second phase amplification reaction is begun. An example of a linear amplification system is "T7-based Linear Amplification of DNA" (TLAD; see Liu et al., BMC Genomics, 4: Art. No. 19, May 9, 2003). Other methods are known, e.g., from U.S. Pat. No. 9,139,870, or disclosed herein. Accordingly, the term "linear amplification" refers to an amplification reaction which does not result in the exponential amplification of a target nucleic acid sequence. The term "linear amplification" does not refer to a method that simply makes a single copy of a nucleic acid strand, such as the transcription of an RNA molecule into a single cDNA molecule as in the first-strand synthesis step of reverse transcription (RT)-PCR.

As used herein, the term "exponential amplification" refers to nucleic acid amplification that is designed to produce an increase in the target nucleic acid geometrically proportional to the amount of target nucleic acid in the reaction. For example, PCR produces one DNA strand for every original target strand and for every synthesized strand present. Similarly, transcription-associated amplification produces multiple RNA transcripts for every original target strand and for every subsequently synthesized strand. The amplification is exponential because the synthesized strands are used as templates in subsequent rounds of amplification. An amplification reaction need not actually produce exponentially increasing amounts of nucleic acid to be considered exponential amplification, so long as the amplification reaction is designed to produce such increases.

"Transcription-associated amplification" or "transcription-mediated amplification" (TMA) refer to nucleic acid amplification that uses an RNA polymerase to produce multiple RNA transcripts from a nucleic acid template. These methods generally employ an RNA polymerase, a DNA polymerase, deoxyribonucleoside triphosphates, ribonucleoside triphosphates, and a template complementary oligonucleotide that includes a promoter sequence, e.g., a T7 promoter, and optionally may include one or more other oligonucleotides. When a T7 promoter-containing oligomer is used, it may be referred to as a "T7 primer" or "T7 oligomer"; other primers/oligomers may be referred to as "non-T7" or "NT7" primers/oligomers. TMA methods and single-primer transcription-associated amplification methods are embodiments of amplification methods used for detection of C1orf43 target sequences as described herein. Variations of transcription-associated amplification are well-known in the art as previously disclosed in detail (see. e.g., U.S. Pat. Nos. 4,868,105; 5,124,246; 5,130,238; 5,399,491; 5,437,990; 5,554,516; and 7,374,885; and International Patent Application Pub. Nos. WO 88/01302; WO 88/10315; and WO 95/03430; each incorporated by reference herein). The person of ordinary skill in the art will appreciate that the disclosed compositions may be used in amplification methods based on extension of oligomer sequences by a polymerase.

As used herein, the term "real-time TMA" refers to single-primer transcription-mediated amplification ("TMA") of target nucleic acid that is monitored through real-time detection.

The term "amplicon" or "amplification product" as used herein refers to the nucleic acid molecule generated during an amplification procedure that is complementary or homologous to a sequence contained within the target sequence. The complementary or homologous sequence of an amplicon is sometimes referred to herein as a "target-specific sequence." Amplicons generated using the amplification oligomers of the current disclosure may comprise non-target specific sequences. Amplicons can be double-stranded or single-stranded and can include DNA, RNA, or both. For example, DNA-dependent RNA polymerase transcribes single-stranded amplicons from double-stranded DNA during transcription-mediated amplification procedures. These single-stranded amplicons are RNA amplicons and can be either strand of a double-stranded complex, depending on how the amplification oligomers are configured. Thus, amplicons can be single-stranded RNA. RNA-dependent DNA polymerases synthesize a DNA strand that is complementary to an RNA template. Thus, amplicons can be double-stranded DNA and RNA hybrids. RNA-dependent DNA polymerases often include RNase activity, or are used in conjunction with an RNase, which degrades the RNA strand. Thus, amplicons can be single stranded DNA. RNA-dependent DNA polymerases and DNA-dependent DNA polymerases synthesize complementary DNA strands from DNA templates. Thus, amplicons can be double-stranded DNA. RNA-dependent RNA polymerases synthesize RNA from an RNA template. Thus, amplicons can be double-stranded RNA. DNA-dependent RNA polymerases synthesize RNA from double-stranded DNA templates, also referred to as transcription. Thus, amplicons can be single stranded RNA. Amplicons and methods for generating amplicons are known to those skilled in the art. For convenience herein, a single strand of RNA or a single strand of DNA may represent an amplicon generated by an amplification oligomer combination of the current disclosure. Such representation is not meant to limit the amplicon to the representation shown. Skilled artisans in possession of the instant disclosure will use amplification oligomers and polymerase enzymes to generate any of the numerous types of amplicons, all within the spirit and scope of the current disclosure.

"Detection probe," "detection oligonucleotide," "probe oligomer," and "detection probe oligomer" are used interchangeably to refer to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., a probe linked to its target via an intermediate molecular structure). Detection probes may be DNA, RNA, analogs thereof or combinations thereof (e.g., DNA/RNA chimerics) and they may be labeled or unlabeled. Detection probes may further include alternative backbone linkages such as, e.g., 2'-O-methyl linkages. A detection probe's "target sequence" generally refers to a smaller nucleic acid sequence region within a larger nucleic acid sequence that hybridizes specifically to at least a portion of a probe oligomer by standard base pairing. A detection probe may comprise target-specific sequences and other sequences that contribute to the three-dimensional conformation of the probe (see. e.g., U.S. Pat. Nos. 5,118,801; 5,312,728; 6,849,412; 6,835,542; 6,534,274; and 6,361,945; and US Patent Application Pub. No. 20060068417; each incorporated by reference herein).

As used herein, a "linear" detection probe, oligomer, or oligonucleotide is a detection oligomer that does not substantially form conformations held by intramolecular bonds, e.g., is configured to hybridize along substantially all of its length to its target sequence and/or lacks a self-complementary segment of 3 or more nucleotides at or near its 5' and 3' ends (such as the terminal 7, 6, 5, or 4 nucleotides do not comprise three consecutive self-complementary nucleotides) that can form a hairpin or other self-hybridized secondary structure.

As used herein, a "label" refers to a moiety or compound joined directly or indirectly to a probe that is detected or leads to a detectable signal. Direct labeling can occur through bonds or interactions that link the label to the probe, including covalent bonds or non-covalent interactions, e.g., hydrogen bonds, hydrophobic and ionic interactions, or formation of chelates or coordination complexes. Indirect labeling can occur through use of a bridging moiety or "linker" such as a binding pair member, antibody, or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Labels may be detectable in a homogeneous assay in which bound labeled probe in a mixture exhibits a detectable change different from that of an unbound labeled probe, e.g., instability or differential degradation properties. A "homogeneous detectable label" can be detected without physically removing bound from unbound forms of the label or labeled probe (see. e.g., U.S. Pat. Nos. 5,283,174; 5,656,207; and 5,658,737; each incorporated by reference herein). Labels include chemiluminescent compounds, e.g., acridinium ester ("AE") compounds that include standard AE and derivatives (see. e.g., U.S. Pat. Nos. 5,656,207; 5,658,737; and 5,639,604; each incorporated by reference herein). Synthesis and methods of attaching labels to nucleic acids and detecting labels are well known. (See. e.g., Sambrook et al. Molecular Cloning. A Laboratory Manual, 2nd ed. (Cold Spring Harbor Laboratory Press, Cold Spring Habor, N Y, 1989), Chapter 10, incorporated by reference herein. See also U.S. Pat. Nos. 5,658,737; 5,656,207; 5,547,842; 5,283,174; and 4,581,333; each incorporated by reference herein). More than one label, and more than one type of label, may be present on a particular probe, or detection may use a mixture of probes in which each probe is labeled with a compound that produces a detectable signal (see. e.g., U.S. Pat. Nos. 6,180,340 and 6,350,579, each incorporated by reference herein).

"Capture probe," "capture oligonucleotide," "capture oligomer," "target capture oligomer," and "capture probe oligomer" are used interchangeably to refer to a nucleic acid oligomer that specifically hybridizes to a target sequence in a target nucleic acid by standard base pairing and joins to a binding partner on an immobilized probe to capture the target nucleic acid to a support. One example of a capture oligomer includes two binding regions: a sequence-binding region (e.g., target-specific portion) and an immobilized probe-binding region, usually on the same oligomer, although the two regions may be present on two different oligomers joined together by one or more linkers. Another embodiment of a capture oligomer uses a target-sequence binding region that includes random or non-random poly-GU, poly-GT, or poly U sequences to bind non-specifically to a target nucleic acid and link it to an immobilized probe on a support.

As used herein, an "immobilized oligonucleotide," "immobilized probe," "immobilized binding partner," "immobilized oligomer," or "immobilized nucleic acid" refers to a nucleic acid binding partner that joins a capture oligomer to a support, directly or indirectly. An immobilized probe joined to a support facilitates separation of a capture probe bound target from unbound material in a sample. One embodiment of an immobilized probe is an oligomer joined to a support that facilitates separation of bound target sequence from unbound material in a sample. Supports may include known materials, such as matrices and particles free in solution, which may be made of nitrocellulose, nylon, glass, polyacrylate, mixed polymers, polystyrene, silane, polypropylene, metal, or other compositions, of which one embodiment is magnetically attractable particles. Supports may be monodisperse magnetic spheres (e.g., uniform size+ 5%), to which an immobilized probe is joined directly (via covalent linkage, chelation, or ionic interaction), or indirectly (via one or more linkers), where the linkage or interaction between the probe and support is stable during hybridization conditions.

"Sample preparation" refers to any steps or method that treats a sample for subsequent amplification and/or detection of nucleic acids present in the sample. Samples may be complex mixtures of components of which the target nucleic acid is a minority component. Sample preparation may include any known method of concentrating components, such as microbes or nucleic acids, from a larger sample volume, such as by filtration of airborne or waterborne particles from a larger volume sample or by isolation of microbes from a sample by using standard microbiology methods. Sample preparation may include physical disruption and/or chemical lysis of cellular components to release intracellular components into a substantially aqueous or organic phase and removal of debris, such as by using filtration, centrifugation or adsorption. Sample preparation may include use of a nucleic acid oligonucleotide that selectively or non-specifically capture a target nucleic acid and separate it from other sample components (e.g., as described in U.S. Pat. No. 6,110,678 and International Patent Application Pub. No. WO 2008/016988, each incorporated by reference herein).

"Separating" or "purifying" means that one or more components of a sample are removed or separated from other sample components. Sample components include target nucleic acids usually in a generally aqueous solution phase, which may also include cellular fragments, proteins, carbohydrates, lipids, and other nucleic acids. "Separating" or "purifying" does not connote any degree of purification. Typically, separating or purifying removes at least 70%, or at least 80%, or at least 95% of the target nucleic acid from other sample components.

As used herein, the terms "TTime," "emergence time," and "time of emergence" are interchangeable and represent the threshold time or time of emergence of signal in a real-time plot of the assay data. TTime values estimate the time at which a particular threshold indicating amplicon production is passed in a real-time amplification reaction. TTime and an algorithm for calculating and using TTime values are described in Light et al., U.S. Pub. No. 2006/0276972, paragraphs [0517] through [0538], the disclosure of which is incorporated by reference herein. A curve fitting procedure is applied to normalized and background-adjusted data. The curve fit is performed for only a portion of the data between a predetermined low bound and high bound. The goal, after finding the curve that fits the data, is to estimate the time corresponding to the point at which the curve or a projection thereof intersects a predefined threshold value. In one embodiment, the threshold for normalized data is 0.11. The high and low bounds are determined empirically as that range over which curves fit to a variety of control data sets exhibit the least variability in the time associated with the given threshold value. For example, in one embodiment, the low bound is 0.04 and the high bound is 0.36. The curve is fit for data extending from the first data point below the low bound through the first data point past the high bound. Next, there is made a determination whether the slope of the fit is statistically significant. For example, if the p value of the first order coefficient is less than 0.05, the fit is considered significant, and processing continues. If not, processing stops. Alternatively, the validity of the data can be determined by the $R^2$ value. The slope m and intercept b of the linear curve y=mx+b are determined for the fitted curve. With that information, TTime can be determined as follows: TTime=(Threshold−b)/m.

References, particularly in the claims, to "the sequence of SEQ ID NO: X" refer to the base sequence of the corresponding sequence listing entry and do not require identity of the backbone (e.g., RNA, 2'-O-Me RNA, or DNA) unless otherwise indicated. Furthermore, T and U residues are to be considered interchangeable for purposes of sequence listing entries unless otherwise indicated, e.g., a sequence can be considered identical to SEQ ID NO: 6 regardless of whether the residue at the seventh position is a T or a U.

C. Oligomers, Compositions, and Kits

The present disclosure provides oligomers, compositions, and kits, useful for amplifying, detecting, or quantifying C1orf43 from a sample.

In some embodiments, amplification oligomers are provided. Amplification oligomers generally comprise a target-hybridizing region, e.g., configured to hybridize specifically to a C1orf43 nucleic acid. While oligomers of different lengths and base composition may be used for amplifying C1orf43 nucleic acids, in some embodiments oligomers in this disclosure have target-hybridizing regions from 10 to 60 bases in length, from 14 to 50 bases in length, or from 15 to 40 bases in length.

In certain embodiments, an amplification oligomer as described herein is a promoter primer further comprising a promoter sequence located 5' to the target-hybridizing sequence and which is non-complementary to the C1orf43 target nucleic acid. For example, in some embodiments of an oligomer combination as described herein for amplification of a C1orf43 target region, an amplification oligomer as described above is a promoter primer further comprising a promoter sequence 5' to the target-hybridizing sequence. Alternatively, an amplification oligomer can be a promoter provider comprising a promoter sequence. In particular embodiments, the promoter sequence is a T7 RNA polymerase promoter sequence such as, for example, a T7 promoter sequence having the sequence shown in SEQ ID NO: 58. In some embodiments, at least one, e.g., two, three, or four promoter primers are provided comprising a target-hybridizing sequence that hybridizes to (+)-strand (coding strand) C1orf43 sequence.

Exemplary target-hybridizing sequences that hybridize to (+)-strand (coding strand) C1orf43 sequence are SEQ ID NOs: 27, 29, 31, and 33. Exemplary promoter-primers that hybridize to (+)-strand (coding strand) C1orf43 sequence are SEQ ID NOs: 26, 28, 30, and 32.

In some embodiments, an amplification oligomer is not a promoter primer or does not comprise a promoter sequence. For example, in PCR-based approaches the primers are generally not promoter primers, and in TMA-based approaches at least one primer that is not a promoter primer is typically used (while at least one promoter primer is also used). In some embodiments, at least one, e.g., two, three, or four amplification oligomers that are not promoter primers are provided comprising a target-hybridizing sequence that hybridizes to (−)-strand (template strand) C1orf43 sequence.

Exemplary target-hybridizing sequences that hybridize to (−)-strand (template strand) C1orf43 sequence are SEQ ID NOs: 34, 35, 36, 37, and 38.

The amplification oligomers discussed above can be used in an amplification reaction configured to produce an amplicon, e.g., comprising C1orf43 sequence such as at least 30, 40, 50, 60, 70, 80, 90, 100, 110, 120, 130, 140, or 144 nucleotides of the sequence of SEQ ID NO: 40; the sequence of SEQ ID NO: 41; or the sequence of SEQ ID NO: 42.

Various embodiments of amplification oligomers, including with respect to their sequences, are disclosed in the summary above, any of which can be combined to the extent feasible with the features discussed above in this section. In some embodiments, at least one probe oligomer is provided. Some embodiments of detection probes that hybridize to complementary amplified sequences may be DNA or RNA oligomers, or oligomers that contain a combination of DNA and RNA nucleotides, or oligomers synthesized with a modified backbone, e.g., an oligomer that includes one or more 2'-methoxy substituted ribonucleotides. Probes used for detection of the amplified C1orf43 sequences may be unlabeled and detected indirectly (e.g., by binding of another binding partner to a moiety on the probe) or may be labeled with a variety of detectable labels. A detection probe oligomer may contain a 2'-methoxy backbone at one or more linkages in the nucleic acid backbone.

In some embodiments, a detection probe oligomer in accordance with the present disclosure further includes a label. Particularly suitable labels include compounds that emit a detectable light signal, e.g., fluorophores or luminescent (e.g., chemiluminescent) compounds that can be detected in a homogeneous mixture. More than one label, and more than one type of label, may be present on a particular probe, or detection may rely on using a mixture of probes in which each probe is labeled with a compound that produces a detectable signal (see. e.g., U.S. Pat. Nos. 6,180,340 and 6,350,579, each incorporated by reference herein). Labels may be attached to a probe by various means including covalent linkages, chelation, and ionic interactions, but in some embodiments the label is covalently attached. For example, in some embodiments, a detection probe has an attached chemiluminescent label such as, e.g., an acridinium ester (AE) compound (see. e.g., U.S. Pat. Nos. 5,185,439; 5,639,604; 5,585,481; and 5,656,744; each incorporated by reference herein), which in typical variations is attached to the probe by a non-nucleotide linker (see. e.g., U.S. Pat. Nos. 5,585,481; 5,656,744; and 5,639,604, each incorporated by reference herein).

A detection probe oligomer in accordance with the present disclosure may further include a non-target-hybridizing sequence. In some applications, probes exhibiting at least some degree of self-complementarity are desirable to facilitate detection of probe: target duplexes in a test sample without first requiring the removal of unhybridized probe prior to detection. Specific embodiments of such detection probes include, for example, probes that form conformations held by intramolecular hybridization, such as conformations generally referred to as hairpins. Particularly suitable hairpin probes include a "molecular torch" (see. e.g., U.S. Pat. Nos. 6,849,412; 6,835,542; 6,534,274; and 6,361,945, each incorporated by reference herein) and a "molecular beacon" (see. e.g., Tyagi et al., supra; U.S. Pat. Nos. 5,118,801 and 5,312,728, supra).

In yet other embodiments, a detection probe is a linear oligomer that does not substantially form conformations held by intramolecular bonds. In some embodiments, the linear detection probe comprises an AE as discussed above. Detection probes comprising an AE, including linear detection probes, can function as flasher probes or glower probes in dual kinetic assays (DKAs). See, e.g., U.S. Pat. No. 5,840,873, which is incorporated by reference herein, for a description of flasher and glower probes and dual kinetic assays.

By way of example of detection oligomers comprising a non-target-hybridizing sequence, structures referred to as "molecular beacons" comprise nucleic acid molecules having a target complementary sequence, an affinity pair (or nucleic acid arms) holding the probe in a closed conformation in the absence of a target nucleic acid sequence, and a label pair that interacts when the probe is in a closed conformation. Hybridization of the target nucleic acid and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are fully described in U.S. Pat. No. 5,925,517, the disclosure of which is hereby incorporated by reference. Molecular beacons useful for detecting C1orf43 nucleic acid sequences may be created by appending to either end of one of the probe (e.g., target-hybridizing) sequences disclosed herein, a first nucleic acid arm comprising a fluorophore and a second nucleic acid arm comprising a quencher moiety. In this configuration, a C1orf43 specific probe sequence disclosed herein serves as the target-complementary "loop" portion of the resulting molecular beacon, while the self-complementary "arms" of the probe represent the "stem" portion of the probe.

Another example of a self-complementary hybridization assay probe that may be used in conjunction with the disclosure is a structure commonly referred to as a "molecular torch" (sometimes referred to simply as a torch). These self-reporting probes are designed to include distinct regions of self-complementarity (coined "the target binding domain" and "the target closing domain") which are connected by a joining region (e.g., a —(CH2)$_9$— linker) and which hybridize to one another under predetermined hybridization assay conditions. When exposed to an appropriate target or denaturing conditions, the two complementary regions (which may be fully or partially complementary) of the molecular torch melt, leaving the target binding domain available for hybridization to a target sequence when the predetermined hybridization assay conditions are restored. Molecular torches are designed so that the target binding domain favors hybridization to the target sequence over the target closing domain. The target binding domain and the target closing domain of a molecular torch include interacting labels (e.g., fluorescent/quencher) positioned so that a different signal is produced when the molecular torch is self-hybridized as opposed to when the molecular torch is hybridized to a target nucleic acid, thereby permitting detection of probe: target duplexes in a test sample in the presence of unhybridized probe having a viable label associated therewith. Molecular torches are fully described in U.S. Pat. No. 6,361,945, the disclosure of which is hereby incorporated by reference.

Molecular torches and molecular beacons in some embodiments are labeled with an interactive pair of detectable labels. Examples of detectable labels that are members of an interactive pair of labels include those that interact with each other by FRET or non-FRET energy transfer mechanisms. Fluorescence resonance energy transfer (FRET) involves the radiationless transmission of energy quanta from the site of absorption to the site of its utilization in the molecule, or system of molecules, by resonance interaction between chromophores, over distances considerably greater than interatomic distances, without conversion to thermal energy, and without the donor and acceptor coming into kinetic collision. The "donor" is the moiety that initially absorbs the energy, and the "acceptor" is the moiety to which the energy is subsequently transferred. In addition to FRET, there are at least three other "non-FRET" energy transfer processes by which excitation energy can be transferred from a donor to an acceptor molecule.

When two labels are held sufficiently close that energy emitted by one label can be received or absorbed by the second label, whether by a FRET or non-FRET mechanism, the two labels are said to be in "energy transfer relationship" with each other. This is the case, for example, when a molecular beacon is maintained in the closed state by formation of a stem duplex, and fluorescent emission from a fluorophore attached to one arm of the probe is quenched by a quencher moiety on the opposite arm.

Exemplary label moieties for the disclosed molecular torches and molecular beacons include a fluorophore and a second moiety having fluorescence quenching properties (i.e., a "quencher"). In this embodiment, the characteristic signal is likely fluorescence of a particular wavelength, but alternatively could be a visible light signal. When fluorescence is involved, changes in emission are in some embodiments due to FRET, or to radiative energy transfer or non-FRET modes. When a molecular beacon having a pair of interactive labels in the closed state is stimulated by an appropriate frequency of light, a fluorescent signal is generated at a first level, which may be very low. When this same probe is in the open state and is stimulated by an appropriate frequency of light, the fluorophore and the quencher moieties are sufficiently separated from each other that energy transfer between them is substantially precluded. Under that condition, the quencher moiety is unable to quench the fluorescence from the fluorophore moiety. If the fluorophore is stimulated by light energy of an appropriate wavelength, a fluorescent signal of a second level, higher than the first level, will be generated. The difference between the two levels of fluorescence is detectable and measurable. Using fluorophore and quencher moieties in this manner, the molecular beacon is only "on" in the "open" conformation and indicates that the probe is bound to the target by emanating an easily detectable signal. The conformational state of the probe alters the signal generated from the probe by regulating the interaction between the label moieties.

Examples of donor/acceptor label pairs that may be used in connection with the disclosure, making no attempt to distinguish FRET from non-FRET pairs, include fluorescein/tetramethylrhodamine, IAEDANS/fluororescein, EDANS/DABCYL, coumarin/DABCYL, fluorescein/fluorescein, BODIPY FL/BODIPY FL, fluorescein/DABCYL, lucifer yellow/DABCYL, BODIPY/DABCYL, eosine/DABCYL, erythrosine/DABCYL, tetramethylrhodamine/DABCYL, Texas Red/DABCYL, CY5/BH1, CY5/BH2, CY3/BH1, CY3/BH2 and fluorescein/QSY7 dye. Those having an ordinary level of skill in the art will understand that when donor and acceptor dyes are different, energy transfer can be detected by the appearance of sensitized fluorescence of the acceptor or by quenching of donor fluorescence. When the donor and acceptor species are the same, energy can be detected by the resulting fluorescence depolarization. Non-fluorescent acceptors such as DABCYL and the QSY7 dyes advantageously eliminate the potential problem of background fluorescence resulting from direct (i.e., non-sensitized) acceptor excitation. Exemplary fluorophore moieties that can be used as one member of a donor-acceptor pair include fluorescein, ROX, and the CY dyes (such as CY5). Exemplary quencher moieties that can be used as another member of a donor-acceptor pair include DABCYL and the BLACK HOLE QUENCHER moieties which are available from Biosearch Technologies, Inc., (Novato, Calif.).

Oligomers that are not intended to be extended by a nucleic acid polymerase, e.g., probe oligomers and capture oligomers, can include a blocker group that replaces the 3' OH to prevent enzyme-mediated extension of the oligomer in an amplification reaction. For example, blocked amplification oligomers and/or detection probes present during amplification in some embodiments do not have a functional 3' OH and instead include one or more blocking groups located at or near the 3' end. A blocking group near the 3' end is in some embodiments within five residues of the 3' end and is sufficiently large to limit binding of a polymerase to the oligomer, and other embodiments contain a blocking group covalently attached to the 3' terminus. Many different chemical groups may be used to block the 3' end, e.g., alkyl groups, non-nucleotide linkers, alkane-diol dideoxynucleotide residues, and cordycepin.

While oligonucleotide probes of different lengths and base composition may be used for detecting C1orf43 nucleic acids, some embodiments of probes in this disclosure are from 10 to 60 bases in length, or between 14 and 50 bases in length, or between 15 and 30 bases in length. A probe oligomer can be provided that is configured to specifically hybridize to the amplicon discussed above.

Exemplary target hybridizing sequences for C1orf43 detection oligomers are SEQ ID NOs: 15, 17, 19, 21, 23, 25, and 59-72. Exemplary molecular torch sequences for detecting a C1orf43 amplicon are SEQ ID NOs: 16, 18, and 20 (e.g., including the features noted in the sequence table including a linker and labels). Exemplary molecular beacon sequences for detecting a C1orf43 amplicon are SEQ ID NOs: 22 and 24 (e.g., including the features noted in the sequence table including labels). Exemplary linear detection probe sequences are SEQ ID NOs: 15 and 59-72. Such linear detection probe sequences are suitable for use in, e.g., hybridization protection and/or dual kinetic assay formats. SEQ ID NO: 69 is an exemplary sequence suitable for use as a glower probe in a DKA. SEQ ID NOs: 15, 59, 68, and 70 are exemplary sequences suitable for use as a flasher probe in a DKA.

Various embodiments of a probe oligomer, including with respect to its sequence, are disclosed in the summary above, any of which can be combined to the extent feasible with the features discussed above in this section.

In some embodiments, at least one capture oligomer is provided, e.g., two, three, or four capture oligomers. It is understood that when two or more capture oligomers are present, their target-hybridizing sequences are different from each other. The one or more capture oligomers comprise a target-hybridizing sequence configured to specifically hybridize to C1orf43 nucleic acid, e.g., from 10 to 60 bases in length, or between 14 and 50 bases in length, or between 15 and 30 bases in length. For example, in specific embodiments, at least one capture probe has the target-hybridizing sequence of SEQ ID NO: 5, 7, 9, 11, or 13. The target-hybridizing sequence is covalently attached to a sequence or moiety that binds to an immobilized probe, e.g., an oligomer attached to a solid substrate, such as a bead.

In more specific embodiments, the capture oligomer includes a tail portion (e.g., a 3' tail) that is not complementary to the C1orf43 target sequence but that specifically hybridizes to a sequence of the immobilized binding partner (e.g., immobilized probe), thereby serving as the moiety allowing the target nucleic acid to be separated from other sample components, such as previously described in, e.g., U.S. Pat. No. 6,110,678, incorporated herein by reference. Any sequence may be used in a tail region, which is can be 5 to 50 nt long, and certain embodiments include a substantially homopolymeric tail ("poly-N sequence") of at least 10 nt, e.g., 10 to 40 nt (e.g., $A_{10}$ to $A_{40}$), such as 14 to 33 nt (e.g., $A_{14}$ to $A_{30}$ or $T_3A_{14}$ to $T_3A_{30}$), that bind to a complementary immobilized sequence (e.g., poly-1) attached to a solid support, e.g., a matrix or particle. For example, in specific embodiments of a capture probe comprising a 3' tail, at least one capture probe has the sequence of SEQ ID NO: 4, 6, 8, 10, or 12.

Various embodiments of capture oligomers, including with respect to its sequence, are disclosed in the summary above, any of which can be combined to the extent feasible with the features discussed above in this section.

Internal control oligomers can be provided, e.g., for confirming that a negative result is valid by establishing that conditions were suitable for amplification. A control template that can be amplified by the control amplification oligomers can also be provided. Control templates may be prepared according to known protocols. See, e.g., U.S. Pat. No. 7,785,844, which is incorporated herein by reference, and which describes an internal control consisting of an in vitro synthesized transcript containing a portion of HIV-1 sequence and a unique sequence targeted by the internal control probe.

In certain aspects of the disclosure, a combination of at least two oligomers is provided for determining the presence or absence of a C1orf43 nucleic acid or quantifying a C1orf43 nucleic acid in a sample. In some embodiments, the C1orf43 nucleic acid is a human C1orf43 nucleic acid. In some embodiments, the C1orf43 nucleic acid is an mRNA, such as a human C1orf43 mRNA. In some embodiments, the oligomer combination includes at least two amplification oligomers suitable for amplifying a target region of a C1orf43 target nucleic acid, e.g., having the sequence of SEQ ID NO: 1, 3, 39, 40, 41, or 42. In such embodiments, at least one amplification oligomer comprises a target-hybridizing sequence in the sense orientation ("sense THS") and at least one amplification oligomer comprises a target-hybridizing sequence in the antisense orientation ("antisense THS"), where the sense THS and antisense THS are each configured to specifically hybridize to a target sequence within a C1orf43sequence. It is understood that the target-hybridizing sequences are selected such that the sequence targeted by antisense THS is situated downstream of the sequence targeted by the sense THS (i.e., the at least two amplification oligomers are situated such that they flank the target region to be amplified).

The oligomers can be provided in various combinations (e.g., kits or compositions) as set forth in the summary above, e.g., comprising 2, 3, or 4 of a first amplification oligomer, second amplification oligomer, probe oligomer, capture oligomer, such as at least one first amplification oligomer and at least one capture oligomer; a first amplification oligomer and a second amplification oligomer, optionally further comprising a probe oligomer; or at least one capture oligomer, a first amplification oligomer, and a second amplification oligomer, optionally further comprising a probe oligomer.

In some embodiments, a combination of oligomers is provided as described below in any of the examples or individual reactions described in the examples.

Also provided by the disclosure is a reaction mixture for determining the presence or absence of a C1orf43 target nucleic acid or quantifying the amount thereof in a sample. A reaction mixture in accordance with the present disclosure comprises at least one or more of the following: an oligomer combination as described herein for amplification of a C1orf43 target nucleic acid; a capture probe oligomer as described herein for purifying the C1orf43 target nucleic acid; and a detection probe oligomer as described herein for determining the presence or absence of a C1orf43 amplification product. In some embodiments, any oligomer combination described above is present in the reaction mixture. The reaction mixture may further include a number of optional components such as, for example, arrays of capture probe nucleic acids. For an amplification reaction mixture, the reaction mixture will typically include other reagents suitable for performing in vitro amplification such as, e.g., buffers, salt solutions, appropriate nucleotide triphosphates (e.g., dATP, dCTP, dGTP, and dTTP; and/or ATP, CTP, GTP and UTP), and/or enzymes (e.g., reverse transcriptase, and/or RNA polymerase), and will typically include test sample components, in which a C1orf43 target nucleic acid may or may not be present. In addition, for a reaction mixture that includes a detection probe together with an amplification oligomer combination, selection of amplification oligomers and detection probe oligomers for a reaction mixture are linked by a common target region (i.e., the reaction mixture will include a probe that binds to a sequence amplifiable by an amplification oligomer combination of the reaction mixture).

Also provided by the subject disclosure are kits for practicing the methods as described herein. A kit in accordance with the present disclosure comprises at least one or more of the following: an amplification oligomer combination as described herein for amplification of a C1orf43 target nucleic acid; at least one capture probe oligomer as described herein for purifying the C1orf43 target nucleic acid; and at least one detection probe oligomer as described herein for determining the presence or absence of a C1orf43 amplification product. In some embodiments, any oligomer combination described above is present in the kit. The kits may further include a number of optional components such as, for example, arrays of capture probe nucleic acids. Other reagents that may be present in the kits include reagents suitable for performing in vitro amplification such as, e.g., buffers, salt solutions, appropriate nucleotide triphosphates (e.g., dATP, dCTP, dGTP, dTTP; and/or ATP, CTP, GTP and UTP), and/or enzymes (e.g., reverse transcriptase, and/or RNA polymerase). Oligomers as described herein may be packaged in a variety of different embodiments, and those skilled in the art will appreciate that the disclosure embraces many different kit configurations. In addition, for a kit that includes a detection probe together with an amplification oligomer combination, selection of amplification oligomers and detection probe oligomers for a kit are linked by a common target region (i.e., the kit will include a probe that binds to a sequence amplifiable by an amplification oligomer combination of the kit). In certain embodiments, the kit further includes a set of instructions for practicing methods in accordance with the present disclosure, where the instructions may be associated with a package insert and/or the packaging of the kit or the components thereof.

D. Methods and Uses

Any method disclosed herein is also to be understood as a disclosure of corresponding uses of materials involved in the method directed to the purpose of the method. Any of the oligomers comprising C1orf43 sequence and any combinations (e.g., kits and compositions) comprising such an oligomer are to be understood as also disclosed for use in detecting or quantifying C1orf43, and for use in the preparation of a composition for detecting or quantifying C1orf43.

Broadly speaking, methods can comprise one or more of the following components: target capture, in which C1orf43 nucleic acid is annealed to a capture oligomer and optionally to an initial amplification oligomer; isolation, e.g., washing, to remove material not associated with a capture oligomer; linear amplification; exponential amplification; and amplicon detection, e.g., amplicon quantification, which may be performed in real time with exponential amplification. Certain embodiments involve each of the foregoing steps. Certain embodiments involve exponential amplification without linear amplification. Certain embodiments involve washing, isolation, and linear amplification. Certain embodiments involve exponential amplification and amplicon detection. Certain embodiments involve any two of the components listed above. Certain embodiments involve any two components listed adjacently above, e.g., washing and linear amplification, or linear amplification and exponential amplification.

In some embodiments, amplification comprises (1) contacting the sample with at least two oligomers for amplifying a C1orf43 nucleic acid target region corresponding to a C1orf43 target nucleic acid, where the oligomers include at least two amplification oligomers as described above (e.g., one or more oriented in the sense direction and one or more oriented in the antisense direction for exponential amplification); (2) performing an in vitro nucleic acid amplification reaction, where any C1orf43 target nucleic acid present in the sample is used as a template for generating an amplification product; and (3) detecting the presence or absence of the amplification product, thereby determining the presence or absence of C1orf43 in the sample, or quantifying the amount of C1orf43 nucleic acid in the sample.

In some embodiments, amplification comprises (1) contacting the sample with at least four oligomers for amplifying a C1orf43 nucleic acid target region corresponding to a C1orf43 target nucleic acid, where the oligomers include at least two amplification oligomers for producing a first amplicon as described above (e.g., one or more oriented in the sense direction and one or more oriented in the antisense direction for exponential amplification) and at least two amplification oligomers for producing a second amplicon as described above (e.g., one or more oriented in the sense direction and one or more oriented in the antisense direction for exponential amplification); (2) performing an in vitro nucleic acid amplification reaction, where any C1orf43 target nucleic acid present in the sample is used as a template for generating an amplification product; and (3) detecting the presence or absence of the first or second amplicons, thereby determining the presence or absence of C1orf43 in the sample, or quantifying the amount of C1orf43 nucleic acid in the sample.

A detection method in accordance with the present disclosure can further include the step of obtaining the sample to be subjected to subsequent steps of the method. In certain embodiments, "obtaining" a sample to be used includes, for example, receiving the sample at a testing facility or other location where one or more steps of the method are performed, and/or retrieving the sample from a location (e.g., from storage or other depository) within a facility where one or more steps of the method are performed.

In certain embodiments, the method further includes purifying the C1orf43 target nucleic acid from other components in the sample, e.g., before an amplification, such as before a capture step. Such purification may include methods of separating and/or concentrating organisms contained in a sample from other sample components, or removing or degrading non-nucleic acid sample components, e.g., protein, carbohydrate, salt, lipid, etc. In some embodiments, DNA in the sample is degraded, e.g., with DNase, and optionally removing or inactivating the DNase or removing degraded DNA.

In particular embodiments, purifying the target nucleic acid includes capturing the target nucleic acid to specifically or non-specifically separate the target nucleic acid from other sample components. Non-specific target capture methods may involve selective precipitation of nucleic acids from a substantially aqueous mixture, adherence of nucleic acids to a support that is washed to remove other sample components, or other means of physically separating nucleic acids from a mixture that contains C1orf43 nucleic acid and other sample components.

Target capture typically occurs in a solution phase mixture that contains one or more capture probe oligomers that hybridize specifically to the C1orf43 target sequence under hybridizing conditions, usually at a temperature higher than the $T_m$ of the tail-sequence: immobilized-probe-sequence duplex. For embodiments comprising a capture probe tail, the C1orf43-target: capture-probe complex is captured by adjusting the hybridization conditions so that the capture probe tail hybridizes to the immobilized probe. Certain embodiments use a particulate solid support, such as paramagnetic beads.

Isolation can follow capture, wherein the complex on the solid support is separated from other sample components. Isolation can be accomplished by any appropriate technique, e.g., washing a support associated with the C1orf43-target-sequence one or more times (e.g., 2 or 3 times) to remove other sample components and/or unbound oligomer. In embodiments using a particulate solid support, such as paramagnetic beads, particles associated with the C1orf43-target may be suspended in a washing solution and retrieved from the washing solution, in some embodiments by using magnetic attraction. To limit the number of handling steps, the C1orf43 target nucleic acid may be amplified by simply mixing the C1orf43 target sequence in the complex on the support with amplification oligomers and proceeding with amplification steps.

Linear amplification can be performed, e.g., by contacting the target nucleic acid sequence with a first phase amplification reaction mixture that supports linear amplification of the target nucleic acid sequence and lacks at least one component that is required for its exponential amplification. In some embodiments, the first phase amplification reaction mixture includes an amplification enzyme selected from a reverse transcriptase, a polymerase, and a combination thereof. The polymerase is typically selected from an RNA-dependent DNA polymerase, a DNA-dependent DNA polymerase, a DNA-dependent RNA polymerase, and a combination thereof. In some embodiments, the first phase amplification reaction mixture further includes a ribonuclease (RNase), such as an RNase H or a reverse transcriptase with an RNase H activity. In some embodiments, the first phase amplification mixture includes a reverse transcriptase with an RNase H activity and an RNA polymerase.

In some embodiments, the first phase amplification mixture may also include an amplification oligonucleotide. The amplification oligonucleotide can include a 5' promoter sequence for an RNA polymerase, such as T7 RNA polymerase, and/or a blocked 3' terminus that prevents its enzymatic extension. In addition, the first phase amplification mixture may sometimes include a blocker oligonucleotide to prevent enzymatic extension of the target nucleic sequence beyond a desired end-point.

As noted above, the key feature of the first phase amplification reaction is its inability to support an exponential amplification reaction because one or more components required for exponential amplification are lacking, and/or an agent is present which inhibits exponential amplification, and/or the temperature of the reaction mixture is not conducive to exponential amplification, etc. Without limitation, the lacking component required for exponential amplification and/or inhibitor and/or reaction condition may be selected from the following group: an amplification oligonucleotide (e.g., an amplification oligonucleotide comprising a 5' promoter sequence for an RNA polymerase, a non-promoter amplification oligonucleotide, or a combination thereof), an enzyme (e.g., a polymerase, such as an RNA polymerase), a nuclease (e.g., an exonuclease, an endonuclease, a cleavase, an RNase, a phosphorylase, a glycosylase, etc), an enzyme co-factor, a chelator (e.g., EDTA or EGTA), ribonucleotide triphosphates (rNTPs), deoxyribonucleotide triphosphates (dNTPs), $Mg^{2+}$, a salt, a buffer, an enzyme inhibitor, a blocking oligonucleotide, pH, temperature, salt concentration and a combination thereof. In some cases, the lacking component may be involved indirectly, such as an agent that reverses the effects of an inhibitor of exponential amplification which is present in the first phase reaction.

Exponentially amplifying a C1orf43 target sequence utilizes an in vitro amplification reaction using at least two amplification oligomers that flank a target region to be amplified.

In some embodiments, at least first and second amplification oligomers as described above are provided. In particular embodiments, the target region to be amplified corresponds to any amplicon discussed above.

Particularly suitable amplification oligomer combinations for amplification of these target regions are described above and in the examples. In some embodiments, the target regions flanked by the first and second amplification oligomers and by the third and fourth amplification oligomers are amplified in the same reaction mixture. Suitable amplification methods include, for example, replicase-mediated amplification, polymerase chain reaction (PCR), ligase chain reaction (LCR), strand-displacement amplification (SDA), and transcription-mediated or transcription-associated amplification (TMA).

For example, some amplification methods that use TMA amplification include the following steps. Briefly, the target nucleic acid that contains the sequence to be amplified is provided as single-stranded nucleic acid (e.g., ssRNA such as C1orf43 mRNA) or is converted to a substantially single-stranded state, e.g., by heat denaturation followed by rapid cooling. Those skilled in the art will appreciate that DNA can be used in TMA; melting of double stranded nucleic acid (e.g., dsDNA) may be used to provide single-stranded target nucleic acids. A promoter primer (e.g., a first amplification oligomer comprising a promoter as described above) binds specifically to the target nucleic acid at its target sequence and a reverse transcriptase (RT) extends the 3' end of the promoter primer using the target strand as a template to create a cDNA extension product, resulting in an RNA: DNA duplex if ssRNA was the original template. Thus, in some embodiments, a cDNA comprising the sequence of a C1orf43 amplicon disclosed herein is produced. An RNase (e.g., RNase H) digests the RNA strand of the RNA: DNA duplex and a second primer binds specifically to its target sequence, which is located on the cDNA strand downstream from the promoter primer end. RT synthesizes a new DNA strand by extending the 3' end of the other primer using the first cDNA template to create a dsDNA that contains a functional promoter sequence. An RNA polymerase specific for the promoter sequence then initiates transcription to produce RNA transcripts that are about 100 to 1000 amplified copies ("amplicons") of the initial target strand in the reaction. Amplification continues when the other primer binds specifically to its target sequence in each of the amplicons and RT creates a DNA copy from the amplicon RNA template to produce an RNA: DNA duplex. RNase in the reaction mixture digests the amplicon RNA from the RNA: DNA duplex and the promoter primer binds specifically to its complementary sequence in the newly synthesized DNA. RT extends the 3' end of the promoter primer to create a dsDNA that contains a functional promoter to which the RNA polymerase binds to transcribe additional amplicons that are complementary to the target strand. The autocatalytic cycles of making more amplicon copies repeat during the course of the reaction resulting in about a billion-fold amplification of the target nucleic acid present in the sample. The amplified products may be detected in real-time during amplification, or at the end of the amplification reaction by using a probe that binds specifically to a target sequence contained in the amplified products. Detection of a signal resulting from the bound probes indicates the presence of the target nucleic acid in the sample.

In some embodiments, the method utilizes a "reverse" TMA reaction. In such variations, the initial or "forward" amplification oligomer is a priming oligonucleotide that hybridizes to the target nucleic acid in the vicinity of the 3'-end of the target region. A reverse transcriptase (RT) synthesizes a cDNA strand by extending the 3'-end of the primer using the target nucleic acid as a template. The other or "reverse" amplification oligomer is a promoter primer or promoter provider having a target-hybridizing sequence configured to hybridize to a target-sequence contained within the synthesized cDNA strand. Where the second amplification oligomer is a promoter primer, RT extends the 3' end of the promoter primer using the cDNA strand as a template to create a second, cDNA copy of the target sequence strand, thereby creating a dsDNA that contains a functional promoter sequence. Amplification then continues essentially as described above in the preceding paragraph for initiation of transcription from the promoter sequence utilizing an RNA polymerase. Alternatively, where the second amplification oligomer is a promoter provider, a terminating oligonucleotide, which hybridizes to a target sequence that is in the vicinity to the 5'-end of the target region, is typically utilized to terminate extension of the priming oligomer at the 3'-end of the terminating oligonucleotide, thereby providing a defined 3'-end for the initial cDNA strand synthesized by extension from the priming oligomer. The target-hybridizing sequence of the promoter provider then hybridizes to the defined 3'-end of the initial cDNA strand, and the 3'-end of the cDNA strand is extended to add sequence complementary to the promoter sequence of the promoter provider, resulting in the formation of a double-stranded promoter sequence. The initial cDNA strand is then used a template to transcribe multiple RNA transcripts complementary to the initial cDNA strand, not including the promoter portion, using an RNA polymerase that recognizes the double-stranded promoter and initiates transcription therefrom. Each of these RNA transcripts is then available to serve as a template for further amplification from the first priming amplification oligomer.

The detection step may be performed using any of a variety of known techniques to detect a signal specifically associated with the target sequence, such as, e.g., by hybridizing the target C1orf43 nucleic acid (e.g., a C1orf43 amplification product) with a labeled detection probe and detecting a signal resulting from the labeled probe. The detection step may also provide additional information on the target sequence, such as, e.g., all or a portion of its nucleic acid base sequence. Detection may be performed after an amplification reaction is completed, or may be performed simultaneously with amplifying the target region, e.g., in real time. Alternatively, detection may be performed on nucleic acid released from cells in a sample, e.g., C1orf43 RNA released by lysing such cells. In one embodiment, the detection step allows homogeneous detection, e.g., detection of the hybridized probe without removal of unhybridized probe from the mixture (see, e.g., U.S. Pat. Nos. 5,639,604 and 5,283,174, each incorporated by reference herein). In some embodiments, the nucleic acids are associated with a surface that results in a physical change, such as a detectable electrical change. Amplified nucleic acids may be detected by concentrating them in or on a matrix and detecting the nucleic acids or dyes associated with them (e.g., an intercalating agent such as ethidium bromide or cyber green), or detecting an increase in dye associated with nucleic acid in solution phase. Other methods of detection may use nucleic acid detection probes that are configured to specifically hybridize to a sequence in the amplified product and detecting the presence of the probe: product complex, or by using a complex of probes that may amplify the detectable signal associated with the amplified products (e.g., U.S. Pat. Nos. 5,424,413; 5,451,503; and 5,849,481; each incorporated by reference herein). Directly or indirectly labeled probes that specifically associate with the amplified product provide a detectable signal that indicates the presence of the target nucleic acid in the sample. In particular, the amplified product will contain a target sequence in or complementary to a sequence in the C1orf43 nucleic acid, and a probe will bind directly or indirectly to a sequence contained in the amplified product to indicate the presence of C1orf43 nucleic acid in the tested sample.

In embodiments that detect the amplified product near or at the end of the amplification step, a linear detection probe may be used to provide a signal to indicate hybridization of the probe to the amplified product. Such detection may use a hybridization protection assay format. For example, such detection may use a luminescently labeled probe that hybridizes to target nucleic acid. Luminescent label is then hydrolyzed from non-hybridized probe. Detection is performed by chemiluminescence using a luminometer (see, e.g., International Patent Application Pub. No. WO 89/002476, incorporated by reference herein). Detection can be multiplexed with detection of an additional target, e.g., using a dual kinetic assay format, in which one of the C1orf43 target and the additional target is detected with a flasher probe (showing relatively fast kinetics (for example, with signal declining substantially from the peak level (e.g., 10-fold) at or before 25 milliseconds following initiation of signal, such as the triggering of a chemiluminescent reaction) and the other of the C1orf43 target and the additional target is detected with a glower probe (showing relatively slow kinetics, for example, with signal continuing at or above 15% of the peak value as of 20 or 25 milliseconds after the peak value occurred and/or distinguishably later than signal from the flasher probe). In other embodiments that use real-time detection, the detection probe may be a hairpin probe such as, for example, a molecular beacon, molecular torch, or hybridization switch probe that is labeled with a reporter moiety that is detected when the probe binds to amplified product. Such probes may comprise target-hybridizing sequences and non-target-hybridizing sequences. Various forms of such probes have been described previously (see, e.g., U.S. Pat. Nos. 5,118,801; 5,312,728; 5,925,517; 6,150,097; 6,849,412; 6,835,542; 6,534,274; and 6,361,945; and US Patent Application Pub. Nos. 20060068417A1 and 20060194240A1; each incorporated by reference herein).

In some embodiments, a molecular torch (sometimes referred to simply as a torch) is used for detection. In some embodiments, the torch is a probe oligomer as disclosed above.

In general, methods involving quantification can involve the step of consulting a standard curve (which can be, e.g., in the form of an equation or graph, including digital representations thereof) that relates pre-amplification amounts of analyte polynucleotide and post-amplification amounts of analyte amplicon.

Since real-time amplification reactions advantageously feature quantitative relationships between the number of analyte polynucleotides input into the reaction and the number of analyte amplicons synthesized as a function of time, the number of analyte polynucleotides present in a test sample can be determined using a standard curve. For example, a plurality of amplification reactions containing known amounts of a polynucleotide standard can be run in parallel with an amplification reaction prepared using a test sample containing an unknown number of analyte polynucleotides. Alternatively, a standard curve can be prepared in advance so that it is unnecessary to prepare a curve each time an analytical procedure is carried out. Such a curve prepared in advance can even be stored electronically in a memory device of a testing instrument. A standard curve having pre-amplification amounts of the polynucleotide standard on a first axis and some indicia of the time required to effect a certain level of nucleic acid amplification (such as a time-of-emergence above a background signal) on a second axis is then prepared. The post-amplification amount of analyte amplicon measured for the test reaction is then located on the post-amplification axis of the standard curve. The corresponding value on the other axis of the curve represents the pre-amplification amount of analyte polynucleotide that was present in the test reaction. Thus, determining the number of molecules of analyte polynucleotide present in the test sample is accomplished by consulting the standard curve, or more particularly by comparing the quantitative results obtained for the test sample with the standard curve, a procedure that will be familiar to those having an ordinary level of skill in the art.

The procedures described herein can be used to quantify analyte polynucleotides (e.g., C1orf43 nucleic acid) present in a test sample. Indeed, if a plurality of standard control amplification reactions are initiated using known numbers of an analyte polynucleotide standard, and if a test reaction that includes an unknown number of analyte polynucleotide molecules is carried out, then it becomes possible after measuring the time required to effect a certain level of amplification in each reaction to determine the number of analyte polynucleotide molecules that must have been present in the test sample. The relationship between the number of analyte polynucleotide molecules input into standard amplification reaction and the time required to effect a certain level of amplification is conveniently established using a graph or an equation corresponding to the graph. Determining the number of analyte polynucleotide molecules present in a test sample is simply a matter of determining from the standard graph or equation the number of analyte polynucleotide molecules that correspond to a measured analyte amplicon signal strength. This illustrates how analyte polynucleotide standards can be used in connection with polynucleotide amplification reactions to quantify pre-amplification amounts of analyte polynucleotide contained in test samples.

Levels can be expressed in various ways, e.g., as concentrations, absolute numbers of copies, mass, emergence time, or RLU or RFU. Levels can be logarithmic or arithmetic. Levels can be converted between different forms of expression. For example, RFU versus time can be converted to an emergence time, and emergence time can be converted to a logarithmic value using a calibration curve. As a further example, the logarithmic value can be converted to an arithmetic value. In some embodiments, a calibration curve or other appropriate standard is used to aid in comparing a level to a predetermined threshold.

In some embodiments, at least one nucleic acid of a microbe or pathogen is detected in addition to a C1orf43 nucleic acid. As shown in the examples, the disclosure provides compositions and methods that do not cross-react with a wide variety of microbes including many pathogens. Accordingly, compositions and methods provided herein are suitable for combination with known methods and compositions for detecting nucleic acids of microbes or pathogens. Exemplary microbes and pathogens include those mentioned below in Example 7. In some embodiments, the nucleic acid of a microbe or pathogen is a human papillomavirus nucleic acid, *Chlamydia trachomatis* nucleic acid, *Neisseria gonorrheae* nucleic acid, *Trichomonas vaginalis* nucleic acid, or *Mycoplasma genitalium* nucleic acid. In some embodiments, the nucleic acid of a microbe or pathogen is a nucleic acid detectable according to a method provided in any one of the *Aptima Combo 2® Assay* (Hologic; Document No. 205446 Rev. 003, March 2017); *The Aptima® Trichomonas vaginalis Assay* (Hologic; Document no. 503684 Rev. 002, July 2017); or the *Aptima Mycoplasma genitalium Assay* (Hologic; Document No. AW-14170-001 Rev. 005, May 2017), each of which are available from Hologic, e.g., via the Hologic website, and which are incorporated herein by reference.

In some embodiments, at least one RNA other than C1orf43 is detected. The cross-reactivity data provided below indicates that compositions and methods according to this disclosure can be highly specific. Accordingly, compositions and methods provided herein are suitable for combination with known methods and compositions for detecting other RNAs, such as other human mRNAs. Exemplary RNAs other than C1orf43 include any RNA suitable for use as an internal control, e.g., for specimen processing and amplification, such as RNA from Bacteriophage MS2; and any RNA proposed for use in calibration in Eisenberg et al., *Trends in Genetics* 29:569-574 (2013) (which is incorporated herein by reference), such as human mRNAs CHMP2A, EMC7, GPI, PSMB2, PSMB4, RAB7A, REEP5, SNRPD3, VCP, and VPS29; additional information and further discussion can be found in Eisenberg et al.

Detection of C1orf43 can be used to validate negative results in methods comprising detection of other nucleic acids by indicating that the sample contained C1orf43-expressing cells, that the steps of the method (e.g., some or all of sample processing, target capture, amplification, and probe detection) were performed properly, and that the reagents used (e.g., enzymes and nucleoside triphosphates) were not compromised.

EXAMPLES

The following examples are provided to illustrate certain disclosed embodiments and are not to be construed as limiting the scope of this disclosure in any way.

General Reagents and Methods. Target capture was performed with a capture oligomer (0.05 pmol/µl) and promoter primer (0.02 pmol/µl) with a sample in a volume of 500 µl. Incubation, isolation, and wash steps were essentially as described in Hologic, Inc., *The Aptima® Trichomonas vaginalis Assay*, Document no. 503684 Rev. 002, July 2017, available on the Hologic website, which is incorporated herein by reference.

Unless otherwise indicated, amplifications were performed isothermally using biphasic transcription-mediated amplification (TMA) with T7 RNA polymerase and reverse transcriptase, in which last primer added in the biphasic procedures was the nonT7 primer. Biphasic TMA was carried out essentially as described in U.S. Pat. No. 9,139,870, which is incorporated herein by reference. During the exponential amplification phase, the promoter primer concentration was 0.05 pmol/µl and the nonT7 and probe oligomer concentrations were each 0.15 pmol/µl.

Detection used molecular torches as probe oligomers which contained a 5'-fluorophore (e.g., FAM or ROX) and a 3'-quencher (e.g., DABCYL) ("5F3D" for FAM and DABCYL or "5R3D" for ROX and DABCYL). Torches are discussed in detail in U.S. Pat. No. 6,849,412, which is incorporated by reference. Torches generally contained a —(CH$_2$)$_9$-linker near the 3'-end (e.g., between the 5$^{th}$ and 6$^{th}$ or between the 4$^{th}$ and 5$^{th}$ nucleotides from the 3'-end). Target capture was performed essentially as described in U.S. Pat. No. 8,034,554, which is incorporated herein by reference.

Separate internal control oligomers and template were used in some experiments to verify reagent presence and activity, etc., and are not specifically discussed below. Exemplary internal control oligomers and template are discussed in U.S. Pat. No. 7,785,844, which is incorporated herein by reference.

Example 1—Amplification and Detection Oligomer Screening

A series of amplification and probe oligomers were designed to evaluate amplification and detection of C1orf43 nucleic acid. Experiments were performed with the following combinations of oligomers.

TABLE 1

Exemplary oligomer combinations.

| Condition | Promoter-primer sequence | nonT7 primer sequence | Probe oligomer sequence |
| --- | --- | --- | --- |
| 1 | SEQ ID NO: 32 | SEQ ID NO: 35 | SEQ ID NO: 14 |
| 2 | SEQ ID NO: 26 | SEQ ID NO: 34 | SEQ ID NO: 14 |
| 3 | SEQ ID NO: 30 | SEQ ID NO: 37 | SEQ ID NO: 14 |
| 4 | SEQ ID NO: 28 | SEQ ID NO: 36 | SEQ ID NO: 14 |
| 5 | SEQ ID NO: 32 | SEQ ID NO: 36 | SEQ ID NO: 14 |
| 6 | SEQ ID NO: 28 | SEQ ID NO: 38 | SEQ ID NO: 14 |
| 1A | SEQ ID NO: 32 | SEQ ID NO: 35 | SEQ ID NO: 21 |
| 2A | SEQ ID NO: 26 | SEQ ID NO: 34 | SEQ ID NO: 21 |
| 3A | SEQ ID NO: 30 | SEQ ID NO: 37 | SEQ ID NO: 21 |
| 4A | SEQ ID NO: 28 | SEQ ID NO: 36 | SEQ ID NO: 21 |
| 5A | SEQ ID NO: 32 | SEQ ID NO: 36 | SEQ ID NO: 21 |
| 6A | SEQ ID NO: 28 | SEQ ID NO: 38 | SEQ ID NO: 21 |
| 1B | SEQ ID NO: 32 | SEQ ID NO: 35 | SEQ ID NO: 16 |
| 2B | SEQ ID NO: 26 | SEQ ID NO: 34 | SEQ ID NO: 16 |
| 3B | SEQ ID NO: 30 | SEQ ID NO: 37 | SEQ ID NO: 16 |
| 4B | SEQ ID NO: 28 | SEQ ID NO: 36 | SEQ ID NO: 16 |
| 5B | SEQ ID NO: 32 | SEQ ID NO: 36 | SEQ ID NO: 16 |
| 6B | SEQ ID NO: 28 | SEQ ID NO: 38 | SEQ ID NO: 16 |

An in vitro transcript (IVT) of C1orf43 was prepared from a DNA having the sequence of SEQ ID NO: 3. Samples were prepared containing the IVT at either $10^4$ or $10^6$ copies (cp) per reaction, along with a negative control lacking the IVT and used directly for amplification, without a capture step.

Amplification and detection results obtained with the exemplary oligomer combinations shown above are given in terms of TTime below (average of duplicates). Negative control results (single replicate except for condition 1 (2 replicates)) were obtained for conditions 1-6 and 2A-6A and were as expected (no false positives; not shown).

TABLE 2

Amplification and detection results with exemplary oligomer combinations.

| Condition | TTime (min), $10^4$ cp IVT | TTime (min), $10^6$ cp IVT |
| --- | --- | --- |
| 1 | 17.67 | 12.14 |
| 2 | 16.82 | 12.62 |
| 3 | 16.28 | 12.08 |
| 4 | 15.64 | 11.55 |
| 5 | 23.24 | 13.72 |
| 6 | 18.09 | 13.64 |
| 1A | 17.50 | 11.75 |
| 2A | 17.04 | 13.05 |
| 3A | 16.07 | 11.97 |
| 4A | 15.40 | 11.42 |
| 5A | 21.12 | 13.60 |
| 6A | 17.41 | 13.52 |
| 1B | 12.60 | 9.16 |
| 2B | 13.85 | 9.71 |
| 3B | 14.96 | 9.02 |
| 4B | 15.51 | 10.12 |
| 5B | 16.68 | 11.10 |
| 6B | 12.85 | 12.01 |

Example 2—Capture Oligomer Screening

Samples were prepared containing $10^2$, $10^3$, $10^4$, or $10^6$ copies per reaction of the IVT described above in Example 1. Target capture was performed in separate experiments using capture oligomers with the following sequences: SEQ ID NO: 4, 10, 8, and 6, followed by amplification and detection of the captured material with an exemplary oligomer combination described above. Results (averages of triplicates) are shown below. Negative control (no IVT) results were obtained for each capture oligomer and were as expected (no false positives; not shown).

TABLE 3

Results with exemplary capture oligomers.

| Capture oligomer | TTime (min) | | | |
|---|---|---|---|---|
| SEQ ID NO | $10^2$ cp IVT | $10^3$ cp IVT | $10^4$ cp IVT | $10^6$ cp IVT |
| 4 | 18.11 | 16.36 | 14.08 | 10.48 |
| 10 | 15.33 | 14.71 | 12.82 | 10.08 |
| 8 | 16.84 | 15.71 | 13.77 | 10.34 |
| 6 | 17.89 | 16.16 | 14.16 | 10.50 |

These results also show that the capture, amplification, and detection of C1orf43 is useful for quantification in that TTime could be linearly regressed against the logarithm of the number of copies to provide a calibration curve (not shown). The calibration curve slope in the different experiments was between about −1.2 and −1.7 $\log_{10}$ copies per minute of TTime.

Example 3—Tissue Type Screening

To confirm the utility of C1orf43 capture, amplification, and detection with samples from various tissues, an exemplary capture oligomer and an exemplary oligomer combination described above were used to capture, amplify, and detect C1orf43 mRNA from total RNA samples from the human tissues listed below. Total RNA samples were obtained from Biochain. All samples were run as a single replicate (1 ng of total RNA per reaction) except for penis (duplicate) and a negative control (triplicate) which gave results as expected (no false positives; not shown). Results, shown as TTime values, were consistent with approximately 10,000 copies of C1orf43 mRNA per sample or more based on calibration data (not shown).

TABLE 4

Results with different tissues.

| Tissue type | TTime (min) |
|---|---|
| Bladder | 11.48 |
| Ductus deferens | 10.65 |
| Epididymis | 10.66 |
| Kidney | 10.71 |
| Lymph node | 12.96 |
| Pancreas | 13.13 |
| Peripheral blood lymphocyte | 13.19 |
| Penis | 11.66 |
| Prostate 1 | 12.45 |
| Seminal vesicle 1 | 11.13 |
| Spleen | 12.45 |
| Seminal vesicle 2 | 12.74 |
| Prostate 2 | 10.59 |

Example 4—Performance with Clinical Vaginal Swab Samples

To confirm the utility of C1orf43 capture, amplification, and detection with clinical samples, an exemplary capture oligomer and an exemplary oligomer combination described above were used to capture, amplify, and detect C1orf43 mRNA from clinical vaginal swab samples.

Vaginal swabs were collected from patients per instructions in the Aptima Unisex Swab Collection Kit for Endocervical and Male Urethral Swab Specimens (Hologic) where the specimen collection swabs are placed immediately in the transport tube which contains a stabilization buffer, the swab shaft is broken off at the score line and the tube is re-capped. The input material from the vaginal swab specimen transport tube is 400 ul of the solution pipetted directly into the assay tube.

All samples were run as a single replicate except for sample 5 (duplicate). Results, shown as TTime values, were consistent with approximately 70,000 copies of C1orf43 mRNA per sample or more for samples 1-13 based on calibration data (not shown).

TABLE 5

Results with clinical vaginal swab samples.

| Vaginal swab sample | TTime (min) |
|---|---|
| 1 | 11.12 |
| 2 | 10.1 |
| 3 | 8.41 |
| 4 | 8.95 |
| 5 | 8.76 |
| 6 | 8.39 |
| 7 | 9.03 |
| 8 | 9.05 |
| 9 | 8.92 |
| 10 | 8.93 |
| 11 | 10.41 |
| 12 | 11.06 |
| 13 | 9.67 |

Example 5—Testing on Processed Urine Samples

To confirm utility with an alternative clinical sample type, fifteen human processed post-DRE urine samples were tested. The urine was collected from patients and processed using the PROGENSA PCA3 Urine Specimen Transport Kit (Gen-Probe/Hologic) where the whole urine sample is added to the urine specimen transport tube which contains PCA3 urine transport medium. The processed urine input for the assay is 400 ul from the specimen tube per assay pipetted into the assay tube. An exemplary capture oligomer and an exemplary oligomer combination described above were used to capture, amplify, and detect C1orf43 mRNA from the processed urine samples.

All samples were run as duplicates, including a negative control (not shown; no false positives). Results, shown as TTime values, were consistent with approximately 50,000 copies of C1orf43 mRNA per sample or more for all tested samples based on calibration data (not shown).

TABLE 6

Results with processed urine samples.

| Whole urine sample | TTime (min) |
|---|---|
| 14 | 15.99 |
| 15 | 15.44 |
| 16 | 15.85 |
| 17 | 15.48 |
| 18 | 16.04 |
| 19 | 15.34 |
| 20 | 14.50 |
| 21 | 15.94 |

TABLE 6-continued

Results with processed urine samples.

| Whole urine sample | TTime (min) |
|---|---|
| 22 | 14.93 |
| 23 | 13.92 |
| 24 | 14.10 |
| 25 | 14.50 |
| 26 | 14.23 |
| 27 | 13.88 |
| 28 | 14.92 |

Example 6—Testing on ThinPrep® Samples

To confirm utility with a further alternative clinical sample type, 197 ThinPrep® clinical samples were tested. ThinPrep® clinical samples are cervical samples processed by immersion in a preservative solution with circulation to remove debris, mucus, and other acellular material followed by cell collection from the solution via filtration for further analysis. The ThinPrep Pap test was used to collect the cervical sample. The ThinPrep liquid cytology specimen vial contains PreservCyt solution which is then prepared for processing with the assay using the Aptima Specimen Transfer Kit where 1 ml of ThinPrep liquid cytology specimen is transferred to the Aptima Specimen Transfer tube which contains ~3 ml sample transport media. The processed ThinPrep sample input for the assay is 400 ul from the specimen tube per assay pipetted into the assay tube.

An exemplary capture oligomer and an exemplary oligomer combination described above were used to capture, amplify, and detect C1orf43 mRNA from the processed ThinPrep® samples.

In all samples, C1orf43 was detected; the low was 22 cp/mL and the high was 263,857 cp/mL. In 75% of the clinical samples the total cps/mL was under 25,000 cp/mL, with the majority being less than 5,000 cp/mL. Mean cp/mL was 22,290 cp/mL. All samples were run as duplicates, including a negative control (not shown; no false positives). Reproducibility was characterized by running 12 of the samples again on a different day with a different reagent batch. The geometric mean observed difference from the first measurement over these 12 samples was 0.15 $\log_{10}$ cp/ml and the range was 0.04-0.32 $\log_{10}$ cp/ml.

Eight negative samples were prepared, starting from preservative solution without cervical material, and no false positive C1orf43 results were observed.

Example 7—Testing of Specificity and Cross-Reactivity

To confirm the specificity of C1orf43 capture, amplification, and detection, the procedure was performed with a series of pools of microbes at high titer ($4.4 \times 10^4$ IFU/ml for *C. trachomatis*; $4.6 \times 10^4$ cells/ml for *T. vaginalis*; $10^4$ TCID$_{50}$/ml for herpes simplex viruses (HSV); $10^6$ copies/ml for HIV; $10^6$ colony forming units/ml for all others). The microbes in each pool were as follows:

Acinetobacter iwoffii, Alcaligenes faecalis, Atopobium vaginae, and Bacteroides fragilis
Campylobacter jejuni, Candida krusei, Candida lusitaniae, and Chlamydia trachomatis
Corynebacterium genitalium, Cryptococcus neoformans, Eggerthella lenta, and Enterobacter cloacae
Enterococcus faecalis, Escherichia coli, Fusobacterium nucleatum, and Haemophilus ducreyi
Klebsiella pneumoniae, Lactobacillus acidophilus, and Lactobacillus iners
Lactobacillus mucosae, Leptotrichia bucalis, Listeria monocytogenes, and Megasphera elsdenii
Mobiluncos cutrisii, Neisseria gonorrheae, Peptostreptococcus magnus, and Prevotella bivia
Propionibacterium acnes, Proteus vulgaris, Pseudomonas aeruginosa, and Staphylococcus aureus
Staphylococcus epidermidis, Streptococcus agalactiae, Streptococcus pyogenes, and Trichomonas vaginalis
Ureaplasma parvum, Ureaplasma urealyticum, and Mycoplasma hominis
Herpes simplex virus I, Herpes simplex virus II, and HIV
Actinomyces israelii
Candida dubliensis, Candida albicans, Candida glabrata, Candida parasilopsis, and Candida tropicalis
Gardnerella vaginalis, Lactobacillus crispatus, Lactobacillus gasseri, and Lactobacillus jensenii.

Testing was negative for C1orf43 for all pools except the pool containing HSV and HIV. HSV and HIV were grown using a human cell line and thus were thought to contain remnants of human nucleic acid including C1orf43.

Example 8—Testing with HPA Detection in Uniplex and Duplex Using an HPV Target Nucleic Acid A number of labeled linear detection probes were synthesized and labeled with an acridinium ester (AE) detectable label for use with a hybridization protection assay (HPA) format. In this example, the linear detection probes were labeled with an AE having fast kinetics, thus configuring the labeled detection probe to function as a flasher probe in a dual kinetic assay (DKA) (see, e.g., U.S. Pat. No. 5,840,873 for a description of flasher/glower probes used with dual kinetic assays). Detection probes comprising the sequences of SEQ ID NOs:15, 59, 68, 69, 70, or 71 were synthesized and labeled with a fast kinetics AE. Each of the six different detection probes were individually added to a reaction well containing 1000 copies per mL of a C1orf43 in vitro transcript. These reaction wells were then placed on a luminometer and the relative light units (RLU) for each AE labeled detection probe was measured over 50 milliseconds. The measured RLU data is presented in Table 7.

TABLE 7

Flasher Probe Kinetics.

| Milliseconds | SEQ ID NO: 15 | SEQ ID NO: 71 | SEQ ID NO: 59 | SEQ ID NO: 70 | SEQ ID NO: 69 | SEQ ID NO: 68 |
|---|---|---|---|---|---|---|
| 1 | — | 0 | 3 | — | — | 1 |
| 2 | 745 | 1,532 | 997 | 548 | 694 | 461 |
| 3 | 6,989 | 10,058 | 7,163 | 4,897 | 5,053 | 4,789 |
| 4 | 17,973 | 20,067 | 15,707 | 11,659 | 10,312 | 12,084 |
| 5 | 24,571 | 24,586 | 20,169 | 15,978 | 12,035 | 16,646 |
| 6 | 23,654 | 24,721 | 19,449 | 18,047 | 11,701 | 18,161 |
| 7 | 20,485 | 21,325 | 18,078 | 18,186 | 11,354 | 17,975 |
| 8 | 17,339 | 18,102 | 15,877 | 16,957 | 10,621 | 17,093 |
| 9 | 14,324 | 14,474 | 13,575 | 15,371 | 9,734 | 15,508 |
| 10 | 12,045 | 11,415 | 11,547 | 13,651 | 8,808 | 13,675 |
| 11 | 10,114 | 9,180 | 9,588 | 11,954 | 7,818 | 11,892 |
| 12 | 8,371 | 7,462 | 8,012 | 10,542 | 6,751 | 10,283 |
| 13 | 6,887 | 6,132 | 6,717 | 9,026 | 6,095 | 8,844 |
| 14 | 5,598 | 4,999 | 5,591 | 7,641 | 5,336 | 7,566 |
| 15 | 4,506 | 4,068 | 4,796 | 6,271 | 4,835 | 6,397 |
| 16 | 3,744 | 3,269 | 4,116 | 5,271 | 4,230 | 5,366 |

TABLE 7-continued

Flasher Probe Kinetics.

| Milliseconds | SEQ ID NO: 15 | SEQ ID NO: 71 | SEQ ID NO: 59 | SEQ ID NO: 70 | SEQ ID NO: 69 | SEQ ID NO: 68 |
|---|---|---|---|---|---|---|
| 17 | 3,054 | 2,669 | 3,431 | 4,408 | 4,218 | 4,466 |
| 18 | 2,550 | 2,192 | 3,050 | 3,674 | 3,973 | 3,809 |
| 19 | 2,106 | 1,801 | 2,563 | 3,164 | 3,523 | 3,271 |
| 20 | 1,765 | 1,496 | 2,267 | 2,669 | 3,446 | 2,735 |
| 21 | 1,480 | 1,229 | 2,006 | 2,245 | 3,137 | 2,320 |
| 22 | 1,227 | 1,040 | 1,758 | 1,942 | 2,957 | 1,958 |
| 23 | 1,043 | 877 | 1,494 | 1,639 | 2,970 | 1,676 |
| 24 | 899 | 755 | 1,406 | 1,375 | 2,867 | 1,431 |
| 25 | 781 | 643 | 1,245 | 1,206 | 2,867 | 1,223 |
| 26 | 684 | 547 | 1,186 | 1,085 | 2,790 | 1,060 |
| 27 | 618 | 471 | 1,091 | 930 | 2,572 | 927 |
| 28 | 540 | 422 | 1,019 | 814 | 2,520 | 816 |
| 29 | 482 | 371 | 1,003 | 745 | 2,417 | 710 |
| 30 | 438 | 333 | 915 | 679 | 2,417 | 648 |
| 31 | 400 | 303 | 890 | 602 | 2,507 | 564 |
| 32 | 367 | 284 | 852 | 548 | 2,276 | 509 |
| 33 | 348 | 258 | 846 | 517 | 2,379 | 455 |
| 34 | 330 | 238 | 799 | 497 | 2,199 | 428 |
| 35 | 299 | 223 | 802 | 464 | 2,122 | 394 |
| 36 | 283 | 213 | 742 | 423 | 2,186 | 363 |
| 37 | 270 | 198 | 755 | 397 | 2,276 | 341 |
| 38 | 250 | 190 | 723 | 380 | 2,160 | 313 |
| 39 | 243 | 182 | 733 | 362 | 2,109 | 302 |
| 40 | 239 | 175 | 698 | 342 | 1,993 | 286 |
| 41 | 221 | 164 | 673 | 317 | 2,122 | 263 |
| 42 | 213 | 167 | 635 | 317 | 2,070 | 255 |
| 43 | 204 | 160 | 657 | 306 | 1,890 | 253 |
| 44 | 198 | 157 | 664 | 296 | 2,057 | 226 |
| 45 | 193 | 146 | 632 | 289 | 2,032 | 218 |
| 46 | 196 | 145 | 629 | 289 | 2,006 | 225 |
| 47 | 189 | 142 | 616 | 279 | 1,774 | 219 |
| 48 | 184 | 143 | 623 | 275 | 2,057 | 206 |
| 49 | 182 | 135 | 619 | 269 | 1,800 | 199 |
| 50 | 176 | 139 | 591 | 260 | 1,929 | 188 |

For DKA, it is preferred that the detection probes labeled with the flasher AE has a fast kinetics so that the flasher signal can be differentiated from the glower signal. The above data show that all labeled detection probes except the labeled detection probe comprising SEQ ID NO:69 have good flasher kinetics because by 25 milliseconds, all RLU values had fallen below 1,300 RLU. Labeled detection probes comprising SEQ ID NOs:15 & 71 showed the best kinetics in this example, having RLU values below 800 at the 25 millisecond time point. These two labeled detection probes were selected for use in a multiplexed assay for the detection of human papilloma virus nucleic acids. It is notable from the above results, that all six labeled detection probes would be useful for a non-DKA format, and further that the labeled detection probe comprising SEQ ID NO:69 may be useful as a glower detection probe in a DKA.

Cellular Controls Using Linear Probes and DKA: A multiplex assay was performed for detecting human papilloma virus and a cellular control in a single reaction well. The assay was performed in DKA format, with a linear detection probe for detecting the cellular control being detectably labeled as a flasher (faster RLU kinetics) and a number of linear detection probes for the detection of various HPV types being labeled as a glower (slower RLU kinetics). For amplifying and detecting C1orf43 from the cellular control, the reaction used one of the detection probes comprising SEQ ID NOs:15 & 71 and labeled with AE moieties, along with a promoter primer comprising the sequence of SEQ ID NO:30 and a non-T7 primer comprising the sequence of SEQ ID NO:34. For amplification and detection of the HPV target nucleic acid, the reaction used the APTIMA HPV Assay (Hologic, Inc., San Diego, Calif.). The internal control was removed from this assay kit.

Samples for this example included SiHa cells and C33A cells (both available from ATCC, Manassas, Va.). SiHa cells comprise both C1orf43 nucleic acids and HPV nucleic acids. C33A cells comprise C1orf43 nucleic acids, but no HPV nucleic acids. The sample conditions were set-up as follows: (i) 1,000 C33A cells per mL, (ii) 10 SiHa cells per mL, (iii) 25 SiHa cells per mL, (iv) 250 SiHa cells per mL, (v) 10 SiHa cells and 100,000 C33A cells per mL, (vi) 25 SiHa cells and 100,000 C33A cells per mL, (vii) 500 SiHa cells and 1,000 C33A cells per mL, and (viii) 250 SiHa cells and 1,000 C33A cells per mL. Condition (i) illustrates amplification and detection of the C1orf43 target nucleic acid. Conditions (ii) to (iv) illustrate amplification and detection of both the C1orf43 target nucleic acid and the HPV nucleic acid. Conditions (v) to (viii) illustrate the amplification and detection of both the C1orf43 target nucleic acid and the HPV nucleic acid in an environment containing a high number of HPV negative cells relative to the number of HPV positive cells. These conditions (v) to (viii) are more similar to a cervical cell swab sample wherein not all collected cells are HPV positive cells. Assays were set-up so that each of SEQ ID NOs:15 & 71 were tested in duplicate against all 8 sample conditions. Multiplex assays were performed as is generally described in the APTIMA HPA Assay instructions for use. Results are shown in Table 8 as RLU data.

TABLE 8

HPV & C1orf43 DKA results.

| Sample condition | AHPV* Assay only. | C1** Assay only. SEQ ID NOs: 15, 30 & 34. | DKA. AHPV Assay. C1 assay SEQ ID NOs: 15, 30 & 34. | DKA. AHPV Assay. C1 assay SEQ ID NOs: 30, 34 & 71. |
|---|---|---|---|---|
| (i): C33A 1,000 cells/mL | 17,148 | 224,242 | 745,073 | 256,117 |
| (ii): 10 SiHa cells/mL | 984,509 | 208,512 | 922,587 | 353,563 |
| (iii): 25 SiHa cells/mL | 915,145 | 315,078 | 1,658,001 | 684,996 |
| (iv): 250 SiHa cells/mL | 1,068,970 | 190,418 | 1,753,484 | 1,228,866 |
| (v): 10 SiHa cells/mL with 100,000 C33A cells/mL | 64,768 | 237,514 | 691,743 | 303,028 |

TABLE 8-continued

HPV & C1orf43 DKA results.

| Sample condition | AHPV* Assay only. | C1** Assay only. SEQ ID NOs: 15, 30 & 34. | DKA. AHPV Assay. C1 assay SEQ ID NOs: 15, 30 & 34. | DKA. AHPV Assay. C1 assay SEQ ID NOs: 30, 34 & 71. |
|---|---|---|---|---|
| (vi): 25 SiHa cells/mL with 100,000 C33A cells/mL | 83,018 | 248,521 | 717,803 | 355,700 |
| (vii): 500 SiHa cells/mL with 1,000 C33A cells/mL | 1,076,716 | 247,809 | 1,766,458 | 1,308,922 |
| (viii): 250 SiHa cells/mL with 1,000 C33A cells/mL | 973,889 | 293,979 | 1,337,878 | 676,534 |

*APTIMA HPV Assay (AHPV Assay).
**C1 Assay (Cellularity Control assay using a labeled detection probe oligomer comprising a sequence of SEQ ID NO: 15 or 71).

These data in Table 8 illustrate a robust and consistent flasher signal for the detection of C1orf43 target nucleic acid using the C1 amplification and detection oligomers comprising sequences of SEQ ID NOs:15, 30, & 34 ("C1 Assay only" column). Table 8 also illustrates similar trends across the sample conditions for each of the AHPV Assay conditions, with or without the presence of the C1 assays. DKA using a labeled detection probe comprising SEQ ID NO:15 provided a more robust signal compared to using a labeled detection probe oligomer comprising SEQ ID NO:71, though both were useful in these assays.

Conclusion: This example illustrates that linear detection probe oligomers are useful in assays for the detection of C1orf43 nucleic acids. Moreover, it is illustrated that these linear detection probe oligomers are useful in multiplexed nucleic acid amplification detection assays, including multiplexed nucleic acid amplification and detection assays wherein two of more of the target nucleic acid types are differentiated by the different probes.

Example 9—ThinPrep Sample Cellularity Control Testing

In this example, a cellularity control assay was performed to determine the concentration of cells in cell collection media. Here, gynecological cell samples were collected at a number of clinical sites using cervical sampling devices. The collected samples were immersed and rinsed in ThinPrep vials filled with 20 mL of a cell preservative solution such as PreservCyt Solution (both the ThinPrep vial and the PreservCyt solution are available from Hologic, Inc., Marlborough, Mass.). The ThinPrep sample vials were then capped and processed using a ThinPrep 5000 processor, generally according to the instructions for use (Hologic, Inc.). ThinPrep sample processing began with a gentle dispersion step to mix the cell sample. The dispersed cell solutions were then captured to a gynecological ThinPrep Pap test filter to collect the cells. The ThinPrep 5000 processor monitors the rate of flow through the ThinPrep Pap test filter during the collection process in order to prevent the cellular presentation from being too scant or too dense. Cell solutions determined to be too scant, typically having less than 250 cells per mL, were marked as having insufficient cellular content. Sample solutions with sufficient cellular content were transferred to a glass slide in a 20 mm-diameter circle, and the slide was automatically deposited into a fixative solution.

Sample Preparation: Seven hundred twenty two (722) cell sample solutions determined to contain insufficient cellular content by the above mentioned processing step were then tested using a cellularity control assay. The cellularity control assay was performed as generally described in the above examples. To test the cell sample solutions, 1 mL of the solution was combined in a transport tube with 2.9 mL of sample transport solution. An in vitro transcript (IVT) and C33A cells were included for use as calibrator reactions. The IVT was prepared by serial dilution of a stock reagent to provide 10,000 copies/mL, 1,000 copies/mL, and 100 copies/mL. The C33A cells were prepared by serial dilution of a stock cell solution to provide 2,500 cells/mL, 1,000 cells/mL, and 100 cells/mL. The serial dilutions for each of the IVT and the C33A calibrator reactions were at a 4 mL total volume.

Assay Set-Up: Oligonucleotides for capture, amplification and detection of the ThinPrep cell samples included a target capture oligonucleotide comprising the sequence of SEQ ID NO:12, a promoter primer comprising the sequence of SEQ ID NO:26, a non-T7 primer comprising the sequence of SEQ ID NO:34, and a detectably labeled hairpin detection probe comprising the sequence of SEQ ID NO:14. The detection probe was labeled with FAM/Dabcyl. Similarly, oligonucleotides were provided for the capture, amplification and detection of the IVT control. Each reaction condition was performed in real time. Assays were performed on a Panther system (Hologic, Inc.).

Results and Conclusions: Of the 722 tested samples, 702 samples were determined as valid (97.2%) by the Panther system. Samples were marked as invalid for a number of reasons, including bubbles in a reaction well. All IVT and C33A reaction wells were determined as valid. The valid samples showed in this assay that 629 were positive (having at least as low as 100 cells/mL) and 73 were negative (having a cell/mL count below the limit of detection). Thus, the cellularity control assay works well to determine the presence or absence of cells in a solution. The cellularity control assay is useful for determining the presence or absence of gynecological cells suspended in a preservative solution, such as the PreservCyt solution. Further, the cellularity control is useful as a reaction control, such as with the C33A control reactions and/or as an assay for determining acceptance or rejection of a solution containing collected cells.

TABLE OF SEQUENCES

In the following table, lower case letters indicate RNA and upper case letters indicate DNA. THS = target hybridizing sequence. X-C9 = -(CH$_2$)$_9$- linker follows position X. 5F3D = 5'-FAM, 3'-DABCYL labels.

| SEQ ID NO | Description | Sequence (5' to 3') |
|---|---|---|
| 1 | C1orf43 (GenBank Accession No. NM_015449.3) | GTGCGCGTGCGCGCCTCGCCACGAGACACCTCTTTCCGGCTCCGGAGTCCTCCTTCACGGCGGCCC TGCCTCCACCACGTGACCACGACGGATGGCCGCCGCCTTCCTCTTACTGTCGTAGTTCCGCTGAGCGCTGACG CTTCCTGGGTGCCATTGCCTGCTCGAGTCACGTGCAGGGGACAGGTCGAAGGCGTCGTTGTTCTCTTCCAGCTG TCCTGCCTGTCCCGCCATGTTTTCAGGCCGGGTCTTGGCTTGGCTTGGTCTTCCCCCGTAAGGAAATGCCGGGAGCTCC AGGGGACCCAGGCGCCTCGCTTCGGCGGAGCCAGGCAGTAACTGGCTCTCGGGCAGTATTGCGGGTAAACCGAACAATT CTGCCGAGGTAGGGAGGCCATGGCGTCGCTAAGGAGATTGATATCTCCAGGGTTCAGGATATCAAGTATGAGCCCA TACGGGACCTGACTTGAAAGAGAGATTGATATCTCCAGGGTTCAGGATATCAAGTATGAGCCCA GCTCCTTGCAGATGATGATGCTAGACTACTACAACTCTGAGATCTCATTCTGAAGGCCGGCATCCCGTTCC ATAGGATGAAAGCTCTGATGCCATTCGTACCTCCTACCTCTGGATCTGCAAAACACTAGTACGCCTTTCAAGGGTACGCAA AGCACTCATTGATACCCTTTTGCAGGACTCTTGCCGTAGATAGAAACAGCCCGCTATGGCACAGGGGTCTTGGCCAGAATGAGT ACCTACGCTATCAGGAGGCCCTGAGTGAGCTGCCACTGCCCTGAGGTCCCCAACACCATCCAGGATTGAAGCACTAGCAT CACCAGTCAGCAGCCAAAGACCTAACTCAGTCCCTGAGGTCCCAACACCCATCCAGGATTGAAGCACTTAAGGATAACATAGACATTGG AGAGTACTCTGTGACGGAGCTGAAGACTCTTGCCGTAGATTAAGCCAGTTGCAATGTGCAAGACAGGCT GCTTGCCGGGCCCCTCGGAACATCTGGCCCCAGCAGCCCAGCAGAACCCTTCCTTATGAGCATTTTTAGAACATTGGCTAAG GAGTTCTTAGAGCTTGTGTCTAAAGGGTAATTCCCCAGCGGTAATTCCTGGATTTGCATTCAGGTGTATTCTTAATGTTTCTGTCAAGCTTC ACTATTTTCCCCAGTAGCGCTTTTTCAGCCATAGTTCACCTTTCCCGTGTTCCAGGTTTATTTATTTAATTCCAAAGGTGAGAG TTAAAAATCTTCACTTGGTTCGAAATCTATACTTTGTGCCAGTGAATTGCCATCTATAATCTGCAGCCTATGTGACAGTAGGAA AGAGTTGATTGATGGAAAAAGCAGAGGAACTGGTGTGGGAGGTCAAGTGGGAAGTTGTGAATGTGGAATAAC TTACCTTTGTGCTCCACTTAAACCAGATGTGTTGCAGCTTTCCTGACATGCAAGGATCTACTTTAATTCCACAC TCTCATTAATAAATTGAATAAAAAGGGAATGTTTTGCACCTGACTCACCACGCTATGTGACAGTAGGAA GGAATGGTTCCCCTAACAAGCCACTGGTCTGACTTTGAACTTTATAATTATAAAATATATCA AATAAAACGTATGAATCAGTCCTTTA |
| 2 | Not Used | |
| 3 | Construct for in vitro transcription with T7 promoter (in bold) | CGACGAAGACTCTCTTTAATACGACTCACTATAGGGAAGCTTGTGCGCGTGCGCCTCGCCACGAGACACCTCT TTCCGGCTCCGCAGTCCTCCTTCACGGCGGCCCTGCCTCCACCACGTGACGCACGGATGGCCGCC GCTTCCTTACTGTGCTAGTTCCGCTGAGCGCTGACGCTTCCTGGGTGCCATTGCCTGAGTCACGT GTCAGGGGAAGCTGAAGGCGTCGTTGTTCTCTTCCAGCTGTCCGCCATGTTTTCAGGCCGGGT CTGCTTGGTCTTCCCCGTAAGGAAATGCCGGGACCCAGGCGCCTCGCTTCGGCGAGC CTGGCGGCTGACCCAGCCAGGCAGCGGGTAAACCCGAACAATTCTGCCGAGGTAGGGAGGCCATGGCGTCCGGAGC AGTAACTGGCTCTCGGGCAGTGTCGTGCTAGACTTCGGAGCCTGGACTTGAAAGAGGAGATTGA TATTCGACTCTCCAGGTTCAGGATATCAAGTATGAGCCCTCCGCCACGTCCTTGCAGATGATGCTAGACTACTAC AACTGGAAACCCAGGGAAATCAAAGTTGCTACAACTATCTGTATAGGATGAAAGCTCTGATGCCATTCGTACC TCTGAGATCTGCAAAACACTAGTACGCCTTTGAAGGCCGATCGTCTTCAGGGCAAGACTCATTGATACCCTTTGGATGGCTATG GAATCTGCGAAACACTAGTACGCCTTTCAGGGCTCATGATTGATACCTTTGGATGGCTATG AAACAGCCCGCTATGGACAGGGGTCTTGGCCAGATGAGTTGCCAGCGACATCACCAGTGAGCTGAGCTG GCCACTGCCGGTTAAAGCACGAATTGGGAGCTCTCAGCGACATCACCAGTCAGCAGCCAAAGACCTAACTCAGTC CCCTGAGGTCTCCCAACCATCCGCCGCCGTCATCCAACACATGC |

TABLE OF SEQUENCES-continued

In the following table, lower case letters indicate RNA and upper case letters indicate DNA. THS = target hybridizing sequence. X-C9 = -(CH$_2$)$_9$- linker follows position X. 5F3D = 5'-FAM, 3'-DABCYL labels.

| SEQ ID NO | Description | Sequence (5' to 3') |
|---|---|---|
| 4 | Capture oligomer | CCAAACAGTTCCCATTCAACTGTCTTTAAAAAAAAAAAAAAAAAAAAAAAAAA |
| 5 | Capture oligomer THS | CCAAACAGTTCCCATTCAACTGTGC |
| 6 | Capture oligomer | CAAAGGUAUAGAUAUGGAAGACAUCUCUUUAAAAAAAAAAAAAAAAAAAAAAAAAAAAA |
| 7 | Capture oligomer THS | CAAAGGUAUAGAUAUGGAAGACAUCUC |
| 8 | Capture oligomer | CUGUGCACAAAGGUAUAGAUAUGGUUUAAAAAAAAAAAAAAAAAAAAAAAAAAAAA |
| 9 | Capture oligomer THS | CUGUGCACAAAGGUAUAGAUAUGG |
| 10 | Capture oligomer | CAUUCAACUGUGCACAAAGGUAUAGUUUAAAAAAAAAAAAAAAAAAAAAAAAAAAAA |
| 11 | Capture oligomer THS | CAUUCAACUGUGCACAAAGGUAUAG |
| 12 | Capture oligomer | CCAAACAGUUCCCAUUCAACUGUGCUUUAAAAAAAAAAAAAAAAAAAAAAAAAAAAA |
| 13 | Capture oligomer THS | CCAAACAGUUCCCAUUCAACUGUGC |
| 14 | C1orf43 molecular torch. 5F3D. Ribonucleotides are 2'-O-methylated. | GUGGAAUAACUUACCUUUGUGCccac |
| 15 | C1orf43 detection oligomer THS | GUGGAAUAACUUACCUUUGUGC |
| 16 | C1orf43 molecular torch. 21-C9. 5F3D. Ribonucleotides are 2'-O-methylated. | GGUCAAGUGGGGAGUUGGUGgacc |
| 17 | C1orf43 detection oligomer THS | GGUCAAGUGGGGAGUUGGUG |
| 18 | C1orf43 molecular torch. 19-C9. 5F3D. Ribonucleotides are 2'-O-methylated. | GGGAAGUUGGUGAAUGUGGuccc |
| 19 | C1orf43 detection oligomer THS | GGGAAGUUGGUGAAUGUGG |
| 20 | C1orf43 molecular torch. 5F3D. Ribonucleotides are 2'-O-methylated. | GGUGAAUGUGGAAUAACUUACCcacc |
| 21 | C1orf43 detection oligomer THS | GGUGAAUGUGGAAUAACUUACC |

TABLE OF SEQUENCES-continued

In the following table, lower case letters indicate RNA and upper case letters indicate DNA. THS = target hybridizing sequence. X-C9 = -(CH$_2$)$_9$- linker follows position X. 5F3D = 5'-FAM, 3'-DABCYL labels.

| SEQ ID NO | Description | Sequence (5' to 3') |
|---|---|---|
| 22 | C1orf43 molecular beacon. 5F3D. Ribonucleotides are 2'-O-methylated. | ggcucGUGGAAUAACUUACCUUUGUGCgagcc |
| 23 | C1orf43 detection oligomer THS | GUGGAAUAACUUACCUUUGUGC |
| 24 | C1orf43 molecular beacon. 5F3D. Ribonucleotides are 2'-O-methylated. | ggcucGGUGAAUGUGGAAUAACUUACCgagcc |
| 25 | C1orf43 detection oligomer THS | GGUGAAUGUGGAAUAACUUACC |
| 26 | C1orf43 promoter primer | AATTTAATACGACTCACTATAGGGAGAGCATGTCAGGAAAGCTGCAACACATCTG |
| 27 | C1orf43 amplification oligomer or amplification oligomer THS | GCATGTCAGGAAAGCTGCAACACATCTG |
| 28 | C1orf43 promoter primer | AATTTAATACGACTCACTATAGGGAGAGCTGCAACACATCTGGTTTAAGTGGAGC |
| 29 | C1orf43 amplification oligomer or amplification oligomer THS | GCTGCAACACATCTGGTTTAAGTGGAGC |
| 30 | C1orf43 promoter primer | AATTTAATACGACTCACTATAGGGAGGAAAGCTGCAACACATCTGGTTTAAG |
| 31 | C1orf43 amplification oligomer or amplification oligomer THS | GGAAAGCTGCAACACATCTGGTTTAAG |
| 32 | C1orf43 promoter primer | AATTTAATACGACTCACTATAGGGAGAGTAGATCCTTGCATGTCAGGAAAGCTGC |
| 33 | C1orf43 amplification oligomer or amplification oligomer THS | GTAGATCCTTGCATGTCAGGAAAGCTGC |
| 34 | C1orf43 amplification oligomer or amplification oligomer THS | GCAGACAGGAACTGGTGGGAG |
| 35 | C1orf43 amplification oligomer or amplification oligomer THS | GGCATCTTTAGAGTTGATTGATGG |
| 36 | C1orf43 amplification oligomer or amplification oligomer THS | CTTAGAGTTGATTGATGGAAAAAGC |
| 37 | C1orf43 amplification oligomer or amplification oligomer THS | GGAAAAAGCAGACAGGAACTG |
| 38 | C1orf43 amplification oligomer or amplification oligomer THS | GCAGACAGGAACTGGTGG |

TABLE OF SEQUENCES-continued

In the following table, lower case letters indicate RNA and upper case letters indicate DNA. THS = target hybridizing sequence. X-C9 = -(CH$_2$)$_9$- linker follows position X. 5F3D = 5'-FAM, 3'-DABCYL labels.

| SEQ ID NO | Description | Sequence (5' to 3') |
|---|---|---|
| 39 | C1orf43 region encompassing exemplary amplicons | GAGATGTCTTCCATATCTATAACCTTTGTGCACAGTTGAATGGGAACTGTTTGGGTTTAGGGCATCTTAGAGTTG<br>ATTGATGAAAAAGCACAGGAACTGGTGGGAGGTCAAGTGGGAAGTTGGTGAATGTGAATAACTTACCTT<br>TGTGCTCCACTTAAACCAGATGTGTTGCAGCTTTCCTGACATGCAAGGATCTAC |
| 40 | Exemplary C1orf43 amplification product | GGCATCTTAGAGTTGATTGATGAAAAAGCAGACAGGAACTGGTGGGAGGTCAAGTGGGAGGTTGGTGAATGT<br>GGAATAACTTACCTTTGTGCTCCACTTAAACCAGATGTGTTGCAGCTTTCCTGACATGCAAGGATCTAC |
| 41 | Exemplary C1orf43 amplification product | GCAGACAGGAACTGGTGGGAGGTCAAGTGGGAGGTTGGTGAATGTGAATAACTTACCTTTGTGCTCCACTTA<br>AACCAGATGTGTTGCAGCTTTCCTGACATGC |
| 42 | Exemplary C1orf43 amplification product | GCAGACAGGAACTGGTGGGAGGTCAAGTGGGAGGTTGGTGAATGTGGAATAACTTACCTTTGTGCTCCACTTA<br>AACCAGATGTGTTGCAGC |
| 43 | C1orf43 region encompassing exemplary detection oligomer hybridization sites | AAAAAGCAGACAGGAACTGGTGGGAGGTCAAGTGGGAAGTTGGTGAATGTGGAATAACTTACCTTTGTGCTCC<br>ACTTAAACCAGATGTGTT |
| 44 | C1orf43 region encompassing exemplary detection oligomer hybridization sites | TCAAGTGGGAAGTTGGTGAATGTGAATAACTTACCTTTGTGCTCCACTTAAAC |
| 45 | C1orf43 region encompassing exemplary detection oligomer hybridization sites | GTCAAGTGGGAAGTTGGTGAATGTGGAATAACTTACCTTTGT |
| 46 | C1orf43 region encompassing exemplary amplification oligomer (e.g., nonT7) hybridization sites | GGCATCTTAGAGTTGATTGATGAAAAAGCAGACAGGAACTGGTGGGAG |
| 47 | exemplary amplification oligomer (e.g., nonT7) core sequence | GCAGACAGGAACTG |
| 48 | exemplary amplification oligomer (e.g., nonT7) core sequence | CTTAGAGTTGATTGATGG |
| 49 | C1orf43 region encompassing exemplary detection oligomer hybridization sites | GGTCAAGTGGGGAAGTTGGTGAATGTGGAATAAACTTACCTTTGTGC |
| 50 | exemplary detection oligomer core sequence | GUGGAAUAACUUACC |
| 51 | exemplary detection oligomer core sequence | GGGGAAGUUGGUG |

TABLE OF SEQUENCES-continued

In the following table, lower case letters indicate RNA and upper case letters indicate DNA. THS = target hybridizing sequence. X-C9 = -(CH₂)₉- linker follows position X. 5F3D = 5'-FAM, 3'-DABCYL labels.

| SEQ ID NO | Description | Sequence (5' to 3') |
|---|---|---|
| 52 | C1orf43 region encompassing exemplary amplification oligomer (e.g., promoter primer) hybridization sites | GTAGATCCTTGCATGTCAGGAAAGCTGCAACACATCTGGTTTAAGTGAGC |
| 53 | Exemplary amplification oligomer (e.g., promoter primer) core sequence | GCTGCAACACATCTG |
| 54 | Exemplary amplification oligomer (e.g., promoter primer) core sequence | GGAAAGCTGC |
| 55 | C1orf43 region encompassing exemplary capture oligomer hybridization sites | CCAAACAGUUCCCAUUCAACUGUGCACAAAGGUAUAGAUAUGGAAGACAUCUC |
| 56 | Exemplary capture oligomer core sequence | CAAAGGUAUAG |
| 57 | Exemplary capture oligomer core sequence | CAUUCAACUGUGC |
| 58 | Exemplary T7 promoter sequence | AATTTAATACGACTCACTATAGGGAGA |
| 59 | C1orf43 linear detection oligomer | GUGAAUGUGGAAUAAACUUAC |
| 60 | C1orf43 linear detection oligomer | GUGGGGAAGUUGGUG |
| 61 | C1orf43 linear detection oligomer | CACCUUAUUGAAUGGAAAC |
| 62 | C1orf43 linear detection oligomer | CUUCAACCACUUACACC |
| 63 | C1orf43 linear detection oligomer | CUUACACCUUAUUGAAUGG |
| 64 | C1orf43 linear detection oligomer | GAAUAACUUACCUUUGUG |
| 65 | C1orf43 linear detection oligomer | CAACCACUUACACCUUAUUG |

TABLE OF SEQUENCES-continued

In the following table, lower case letters indicate RNA and upper case letters indicate DNA. THS = target hybridizing sequence. X-C9 = -(CH$_2$)$_9$- linker follows position X. 5F3D = 5'-FAM, 3'-DABCYL labels.

| SEQ ID NO | Description | Sequence (5' to 3') |
|---|---|---|
| 66 | C1orf43 linear detection oligomer | GAAGUUGGUGAUGUG |
| 67 | C1orf43 linear detection oligomer | GUGGAAUAACUUACCUUUG |
| 68 | C1orf43 linear detection oligomer | GUGGGGAAGUUGGUGAAUG |
| 69 | C1orf43 linear detection oligomer | GAAUGUGGAAUAAC |
| 70 | C1orf43 linear detection oligomer | CUUACCUUUGUGCUCCAC |
| 71 | C1orf43 linear detection oligomer | GAAUAACUUACCUUUGUGCUC |
| 72 | C1orf43 linear detection oligomer | GUCAAGUGGGGAAGUUG |

What is claimed is:

1. A method of detecting the presence or absence of a C1orf43 nucleic acid in a sample, comprising:
    contacting the sample with a combination of oligomers comprising at least first and second amplification oligomers,
    performing a nucleic acid amplification reaction which produces at least a first amplicon in the presence of the C1orf43 nucleic acid,
    and detecting the presence or absence of the first amplicon,
    wherein:
    the first amplicon is produced through extension of the first and second amplification oligomers in the presence of the C1orf43 nucleic acid; and
    wherein the first and second amplification oligomers are reverse and forward amplification oligomers, respectively; and are configured to
    specifically hybridize to first and second sites in the sequence of SEQ ID NO: 39, respectively, wherein the first site is in the complement of SEQ ID NO: 52 and the first amplification oligomer comprises the sequence of SEQ ID NO:53 or SEQ ID NO:54; and
    wherein the second site is in the complement of SEQ ID NO: 46 and the second amplification oligomer comprises the sequence of SEQ ID NO: 47 or SEQ ID NO:48.

2. The method of claim 1, wherein at least one of the amplification oligomers is a promoter-primer.

3. The method of claim 2, wherein the first amplification oligomer is a promoter-primer.

4. The method of claim 3, wherein the promoter-primer comprises a T7 promoter which is located 5' of a target-hybridizing sequence and wherein the T7 promoter comprises the sequence of SEQ ID NO: 58.

5. The method of claim 2, wherein the first amplification oligomer comprises a target-hybridizing sequence comprising the sequence of SEQ ID NO: 27, 29, 31, or 33.

6. The method of claim 5, wherein the first amplification oligomer comprises the sequence of SEQ ID NO: 26, 28, 30, or 32.

7. The method of claim 1, wherein the second amplification oligomer comprises a target-hybridizing sequence comprising the sequence of SEQ ID NO: 34, 35, 36, 37, or 38.

8. The method of claim 1, wherein the combination further comprises at least one probe oligomer that comprises at least 10 nucleotides and is configured to specifically hybridize to an amplicon produced from the first and second amplification oligomers.

9. The method of claim 8, wherein the probe oligomer is configured to specifically hybridize to a detection site in a nucleic acid having the sequence of SEQ ID NO: 49 and wherein the probe oligomer comprises a target hybridizing sequence comprising the sequence of SEQ ID NO: 50 or SEQ ID NO:51.

10. The method of claim 8, wherein the probe oligomer comprises a target hybridizing sequence comprising the sequence of SEQ ID NO: 15, 17, 19, 21, 23, or 25, with up to two mismatches.

11. The method of claim 10, wherein the probe oligomer comprises the sequence of SEQ ID NO: 14, 16, 18, 20, 22, or 24.

12. The method of claim 8, wherein the probe oligomer comprises a target hybridizing sequence comprising the sequence of SEQ ID NO: 59, 60, 64, 66, 67, 68, 69, 70, 71, or 72, with up to two mismatches.

13. The method of claim 8, wherein the probe oligomer comprises 2'-O-methyl-ribose in its backbone.

14. The method of claim 13, wherein at least half, at least 90%, or all of the sugars in the probe oligomer are 2'-O-methyl-ribose.

15. The method of claim 8, wherein at least one probe oligomer comprises a non-nucleotide detectable label.

16. The method of claim 15, wherein the non-nucleotide detectable label is a fluorescent label.

17. The method of claim 16, wherein the probe oligomer comprises a quencher.

18. The method of claim 15, wherein the non-nucleotide detectable label is a chemiluminescent label.

19. A method of isolating C1orf43 nucleic acid from a sample, comprising:
    contacting the sample with at least one capture oligomer under conditions permissive for forming one or more complexes of a capture oligomer and the C1orf43 nucleic acid, thereby forming a composition, wherein the capture oligomer comprises a target hybridizing sequence comprising the sequence of SEQ ID NO: 56 or SEQ ID NO:57 and is configured to specifically hybridize to a capture site in the sequence of SEQ ID NO: 55; and
    isolating the capture oligomer from the composition.

20. The method, of claim 19, wherein the capture oligomer comprises a target hybridizing sequence comprising the sequence of SEQ ID NO: 5, 7, 9, 11, or 13.

21. The method of claim 20, wherein the capture oligomer comprises the sequence of SEQ ID NO: 4, 6, 8, 10, or 12.

* * * * *

UNITED STATES PATENT AND TRADEMARK OFFICE
CERTIFICATE OF CORRECTION

PATENT NO. : 11,377,688 B2
APPLICATION NO. : 16/763387
DATED : July 5, 2022
INVENTOR(S) : Siobhán Miick et al.

It is certified that error appears in the above-identified patent and that said Letters Patent is hereby corrected as shown below:

In the Specification

In Column 10, Line 66, delete "Neisseria gonorrheae" and insert -- Neisseria gonorrhoeae --, therefor.
In Column 11, Line 47, delete "measureable" and insert -- measurable --, therefor.
In Column 12, Line 51, delete "deoxygaunosine," and insert -- deoxyguanosine, --, therefor.
In Column 14, Line 10, delete "processes" and insert -- process --, therefor.
In Column 22, Line 60, delete "probe: target" and insert -- probe:target --, therefor.
In Column 23, Line 30, delete "useful" and insert -- are useful --, therefor.
In Column 23, Line 63, delete "probe: target" and insert -- probe:target --, therefor.
In Column 24, Line 59, delete "IAEDANS/fluororescein," and insert -- IAEDANS/ fluorescein, --, therefor.
In Column 26, Line 14, delete "is can be" and insert -- can be --, therefor.
In Column 26, Line 19, delete "(e.g., poly-1)" and insert -- (e.g., poly-T) --, therefor.
In Column 29, Line 35, delete "tail-sequence: immobilized" and insert
-- tail-sequence:immobilized --, therefor.
In Column 29, Line 37, delete "C1orf43-target: capture" and insert -- C1orf43-target:capture --, therefor.
In Column 31, Line 12, delete "RNA: DNA" and insert -- RNA:DNA --, therefor.
In Column 31, Line 25, delete "RNA: DNA" and insert -- RNA:DNA --, therefor.
In Column 31, Line 27, delete "RNA: DNA" and insert -- RNA:DNA --, therefor.
In Column 32, Line 6, delete "used a" and insert -- used as a --, therefor.
In Column 32, Line 42, delete "probe: product" and insert -- probe:product --, therefor.
In Column 33, Line 2, delete "(for" and insert -- for --, therefor.
In Column 34, Line 44, delete "Neisseria gonorrheae" and insert -- Neisseria gonorrhoeae --, therefor.
In Column 39, Line 62, delete "Acinetobacter iwoffii," and insert -- Acinetobacter Iwoffii, --, therefor.
In Column 40, Line 5, delete "Leptotrichia bucalis," and insert -- Leptotrichia buccalis, --, therefor.
In Column 39, Line 62, delete "Acinetobacter iwoffii," and insert -- Acinetobacter Iwoffii, --, therefor.
In Column 40, Line 5, delete "Leptotrichia bucalis," and insert -- Leptotrichia buccalis, --, therefor.
In Column 40, Line 6, delete "Megasphera elsdenii" and insert -- Megasphaera elsdenii --, therefor.

Signed and Sealed this
Twenty-second Day of October, 2024

Katherine Kelly Vidal
*Director of the United States Patent and Trademark Office*

CERTIFICATE OF CORRECTION (continued)
U.S. Pat. No. 11,377,688 B2

In Column 40, Line 7, delete "Mobiluncos cutrisii, Neisseria gonorrheae," and insert -- Mobiluncus curtisii, Neisseria gonorrhoeae, --, therefor.
In Column 40, Line 18, delete "Candida dubliensis," and insert -- Candida dubliniensis, --, therefor.
In Column 40, Line 19, delete "Candida parasilopsis," and insert -- Candida parapsilosis, --, therefor.
In Column 43, Line 41, delete "two of more" and insert -- two or more --, therefor.
In Columns 51 & 52, in TABLE OF SEQUENCES-continued, Line 13, delete "Clorf43" and insert -- C1orf43 --, therefor.
In Columns 51 & 52, in TABLE OF SEQUENCES-continued, Line 16, delete "Clorf43" and insert -- C1orf43 --, therefor.
In Columns 51 & 52, in TABLE OF SEQUENCES-continued, Line 19, delete "Clorf43" and insert -- C1orf43 --, therefor.
In Columns 51 & 52, in TABLE OF SEQUENCES-continued, Line 22, delete "Clorf43" and insert -- C1orf43 --, therefor.
In Columns 53 & 54, in TABLE OF SEQUENCES-continued, Line 6, delete "Clorf43" and insert -- C1orf43 --, therefor.
In Columns 53 & 54, in TABLE OF SEQUENCES-continued, Line 35, delete "seqeunce" and insert -- sequence --, therefor.
In Columns 53 & 54, in TABLE OF SEQUENCES-continued, Line 37, delete "seqeunce" and insert -- sequence --, therefor.

In the Claims

In Column 91, Lines 34-38, in Claim 1, delete "specifically............54; and" and insert the same at Line 33, after "to", as a continuation subpoint.
In Column 92, Lines 58, in Claim 20, delete "method," and insert -- method --, therefor.